US009068020B2

(12) United States Patent
Yu et al.

(10) Patent No.: US 9,068,020 B2
(45) Date of Patent: Jun. 30, 2015

(54) CD133 EPITOPES

(75) Inventors: John S. Yu, Los Angeles, CA (US);
Keith L. Black, Los Angeles, CA (US);
Gentao Liu, Shanghai (CN)

(73) Assignee: Cedars-Sinai Medical Center, Los Angeles, CA (US)

( * ) Notice: Subject to any disclaimer, the term of this patent is extended or adjusted under 35 U.S.C. 154(b) by 267 days.

(21) Appl. No.: 12/552,945

(22) Filed: Sep. 2, 2009

(65) Prior Publication Data
US 2010/0135975 A1 Jun. 3, 2010

Related U.S. Application Data

(60) Provisional application No. 61/190,718, filed on Sep. 2, 2008.

(51) Int. Cl.
A61K 39/00 (2006.01)
C07K 14/705 (2006.01)
C07K 7/06 (2006.01)
A61K 45/06 (2006.01)

(52) U.S. Cl.
CPC ........ *C07K 14/70596* (2013.01); *A61K 39/0011* (2013.01); *C07K 7/06* (2013.01); *A61K 45/06* (2013.01)

(58) Field of Classification Search
USPC ....................................... 424/184.1
See application file for complete search history.

(56) References Cited

U.S. PATENT DOCUMENTS

| | | | |
|---|---|---|---|
| 4,690,915 A | 9/1987 | Rosenberg | |
| 4,844,893 A | 7/1989 | Honsik et al. | |
| 5,635,363 A | 6/1997 | Altman et al. | |
| 5,643,786 A | 7/1997 | Cohen et al. | |
| 5,788,963 A | 8/1998 | Murphy et al. | |
| 5,831,016 A | 11/1998 | Wang et al. | |
| 5,843,448 A | 12/1998 | Chen et al. | |
| 5,843,633 A | 12/1998 | Yin et al. | |
| 5,844,075 A | 12/1998 | Kawakami et al. | |
| 5,846,538 A | 12/1998 | Cheever et al. | |
| 5,849,589 A | 12/1998 | Tedder et al. | |
| 5,851,756 A | 12/1998 | Steinman et al. | |
| 5,869,445 A | 2/1999 | Cheever et al. | |
| 5,876,712 A | 3/1999 | Cheever et al. | |
| 5,925,729 A | 7/1999 | Boon et al. | |
| 5,994,126 A | 11/1999 | Steinman et al. | |
| 6,010,905 A | 1/2000 | Cohen et al. | |
| 6,015,567 A | 1/2000 | Hudziak et al. | |
| 6,037,135 A | 3/2000 | Kubo et al. | |
| 6,077,519 A | 6/2000 | Storkus et al. | |
| 6,248,329 B1* | 6/2001 | Chandrashekar et al. | 424/191.1 |
| 6,300,090 B1 | 10/2001 | Steinman et al. | |
| 6,455,678 B1 | 9/2002 | Yin et al. | |
| 6,458,585 B1 | 10/2002 | Vachula et al. | |
| 6,479,286 B1 | 11/2002 | Nelson et al. | |
| 6,482,405 B1 | 11/2002 | Tahara et al. | |
| 6,514,942 B1 | 2/2003 | Ioannides et al. | |
| 6,537,560 B1 | 3/2003 | Kawakami et al. | |
| 6,566,395 B1 | 5/2003 | Moran | |
| 6,632,459 B2 | 10/2003 | Graus et al. | |
| 6,984,522 B2 | 1/2006 | Clarke et al. | |
| 7,115,360 B2 | 10/2006 | Clarke et al. | |
| 7,186,409 B2 | 3/2007 | Snyder et al. | |
| 7,204,982 B2 | 4/2007 | Liau | |
| 7,247,480 B2 | 7/2007 | Waldmann et al. | |
| 7,311,916 B2 | 12/2007 | Wild et al. | |
| 7,338,929 B2 | 3/2008 | Debinski et al. | |
| 7,368,531 B2 | 5/2008 | Rosen et al. | |
| 7,402,314 B2 | 7/2008 | Sherman et al. | |
| 7,504,490 B1 | 3/2009 | Weinstock et al. | |
| 7,842,466 B1 | 11/2010 | Kim et al. | |
| 8,097,256 B2 | 1/2012 | Yu et al. | |
| 8,129,184 B2* | 3/2012 | Yu | 435/368 |
| 8,168,586 B1 | 5/2012 | Fang et al. | |
| 8,383,768 B2* | 2/2013 | Singh et al. | 530/300 |
| 8,604,167 B2* | 12/2013 | Singh et al. | 530/328 |
| 8,871,211 B2 | 10/2014 | Yu et al. | |
| 2002/0034819 A1 | 3/2002 | Smith et al. | |
| 2002/0045261 A1 | 4/2002 | Snyder et al. | |
| 2002/0076707 A1 | 6/2002 | Mack et al. | |
| 2002/0115213 A1 | 8/2002 | Snyder et al. | |
| 2002/0119121 A1 | 8/2002 | Vitiello et al. | |
| 2002/0182194 A1 | 12/2002 | Ju et al. | |

(Continued)

FOREIGN PATENT DOCUMENTS

WO WO 89/06692 7/1989
WO WO 92/20356 11/1992

(Continued)

OTHER PUBLICATIONS

Yu et al., Journal of immunotherapy Nov.-Dec. 2008, pp. 928. CD133 as a Potential Target of Anti-cancer Stem Cell Immunotherapy: Identification of an HLA-A*02 Restricted CD133 Epitope. Abstract.*
Rudinger, J., "Characteristics of the amino acids as components of a peptide hormone sequence",in Peptide Hormones, University Park Press: Baltimore, MD, pp. 1-7, 1976.*
Ngo, J. et al., "Computational Complexity, Protein Structure Prediction, and the Levinthal Paradox", 1994, The Protein Folding Problem and Tertiary Structure Prediction, Merz et al. (eds.), Birkhauser Boston: Boston, MA, pp. 433 and 492-495.*
Voet, Biochemistry John Wiley and Sons, 1990, pp. 126-128.*
Ahmed et al ., HER2-Specific T Cells Target Primary Glioblastoma Stem Cells and Induce Regression of Autologous Experimental TumorsClin Cancer Res; 16(2); 474-85.*
Burg et al., Immunogenicity of Peptides Bound to MHC Class I Molecules Depends on the MHC-Peptide Complex Stabilityl the Journal of Immuno/ogy, 1996, 156; 3308-3314.*

(Continued)

*Primary Examiner* — Maria Leavitt
(74) *Attorney, Agent, or Firm* — Fish & Richardson P.C.

(57) ABSTRACT

An immunogen includes an isolated peptide of 800 amino acid residues or fewer having the amino sequence ILSAFS-VYV (SEQ ID NO:1) with four or fewer amino acid substitutions, a superagonist variant of SEQ ID NO:1, or an amino acid sequence having the formula: (I/K/T/V/M)-L-(S/L)-(A/E/N/D/Q)-(F/V)-(S/M/V/I)-(V/D/R/G/H)-Y-(V/I/L) (SEQ ID NO:13). The immunogens can be used in compositions and in the treatment of disorders.

32 Claims, 4 Drawing Sheets

(56) References Cited

U.S. PATENT DOCUMENTS

| | | |
|---|---|---|
| 2002/0192211 A1 | 12/2002 | Hudziak et al. |
| 2003/0064916 A1 | 4/2003 | Sherman |
| 2003/0095955 A1 | 5/2003 | Noessner et al. |
| 2003/0185823 A1 | 10/2003 | Lum et al. |
| 2003/0190682 A1 | 10/2003 | Law et al. |
| 2003/0202963 A1 | 10/2003 | Crystal et al. |
| 2003/0204052 A1 | 10/2003 | Herrmann et al. |
| 2003/0204071 A1 | 10/2003 | Moore et al. |
| 2004/0057935 A1 | 3/2004 | Yu et al. |
| 2004/0072246 A1 | 4/2004 | Martin et al. |
| 2004/0121946 A9 | 6/2004 | Fikes et al. |
| 2004/0197903 A1 | 10/2004 | Pestano |
| 2004/0203143 A1 | 10/2004 | Tjoa et al. |
| 2005/0059151 A1 | 3/2005 | Bosch |
| 2005/0119198 A1 | 6/2005 | Carmeliet et al. |
| 2005/0169897 A1 | 8/2005 | Snyder et al. |
| 2006/0003323 A1 | 1/2006 | Alsobrook et al. |
| 2006/0204509 A1 | 9/2006 | Harty et al. |
| 2007/0020297 A1 | 1/2007 | Wheeler et al. |
| 2007/0098776 A1 | 5/2007 | Fikes et al. |
| 2007/0167375 A1 | 7/2007 | Okada et al. |
| 2008/0076904 A1 | 3/2008 | Cheever et al. |
| 2008/0107668 A1 | 5/2008 | Philip et al. |
| 2008/0131448 A1 | 6/2008 | Debinski et al. |
| 2008/0166374 A1 | 7/2008 | Debinski et al. |
| 2008/0199484 A1 | 8/2008 | Yu et al. |
| 2008/0206286 A1 | 8/2008 | Yu |
| 2008/0311141 A1 | 12/2008 | Yu et al. |
| 2008/0311142 A1 | 12/2008 | Yu et al. |
| 2009/0093052 A1 | 4/2009 | Yin et al. |
| 2009/0110702 A1 | 4/2009 | Wu et al. |
| 2009/0305418 A1 | 12/2009 | Moriarty et al. |
| 2010/0040637 A1 | 2/2010 | Van Orden et al. |
| 2010/0135975 A1 | 6/2010 | Yu et al. |
| 2010/0310643 A1* | 12/2010 | Singh et al. .......... 424/450 |
| 2012/0052080 A1 | 3/2012 | Okada et al. |
| 2012/0156232 A1 | 6/2012 | Yu et al. |
| 2012/0189664 A1 | 7/2012 | Yu |
| 2012/0231030 A1 | 9/2012 | Derouazi et al. |
| 2013/0115279 A1 | 5/2013 | Singh et al. |
| 2013/0183328 A1 | 7/2013 | Yu et al. |
| 2013/0183378 A1 | 7/2013 | Yu et al. |
| 2014/0234350 A1 | 8/2014 | Yu et al. |
| 2014/0234351 A1 | 8/2014 | Yu et al. |

FOREIGN PATENT DOCUMENTS

| | | |
|---|---|---|
| WO | WO 94/26293 | 11/1994 |
| WO | WO 95/21862 | 8/1995 |
| WO | WO 96/18409 | 6/1996 |
| WO | WO 00/24778 | 5/2000 |
| WO | WO 00/38730 | 7/2000 |
| WO | WO 00/66713 | 11/2000 |
| WO | WO 01/08636 | 2/2001 |
| WO | WO 01/41741 | 6/2001 |
| WO | WO 01/58479 | 8/2001 |
| WO | WO 01/68148 | 9/2001 |
| WO | WO 02/068474 | 9/2002 |
| WO | WO 03/010301 | 2/2003 |
| WO | WO 03/014335 | 2/2003 |
| WO | WO 03/035004 | 5/2003 |
| WO | WO 03/066097 | 8/2003 |
| WO | WO 03/092717 | 11/2003 |
| WO | WO 2005/037995 | 4/2005 |
| WO | WO 2005/043155 | 5/2005 |
| WO | WO 2005/079581 | 9/2005 |
| WO | WO 2006/034334 | 3/2006 |
| WO | WO 2007/062138 | 5/2007 |
| WO | WO 2008/039874 | 4/2008 |
| WO | WO 2008/039969 | 4/2008 |
| WO | WO 2008/039974 | 4/2008 |
| WO | 2008/054716 | 5/2008 |
| WO | WO 2008/052740 | 5/2008 |
| WO | WO 2008/083949 | 7/2008 |
| WO | WO 2010/028066 | 3/2010 |
| WO | WO 2010/129895 | 11/2010 |
| WO | WO 2012/079000 | 6/2012 |

OTHER PUBLICATIONS

Feng et al P55, an Immunogenic but Nonprotective 55-Kilodalton Borrelia burgdorferi Protein in Murine Lyme Disease Infection and Immunity, Jan. 1996, p. 363-365.*

Zhang et al Extensively cross-reactive anti-HIV-1 neutralizing antibodies induced by gp140 immunization PNAS | Jun. 12, 2007 | vol. t04 | No. 24 | 1019).-10198.*

Ji et al., Identification of Novel Human Leukocyte Antigen-A*0201-Restricted, Cytotoxic T Lymphocyte Epitopes on CD133 for Cancer Stem Cell Immunotherapy Medicine 2014;3:356-364.*

Ludewig et al., Adoptive Immunotherapy: Methods and Protocols Non-self MHC-restricted CTL 2005 Human Press Inc. pp 216-217.*

Akasaki et al., "Antitumor effect of immunizations with fusions of dendritic and glioma cells in a mouse brain tumor model," J. Immunother., 24:106-113 (2001).

Akasaki et al., "Dendritic cell-based immunotherapy for malignant gliomas," Expert Rev. Neurother., 5:497-508 (2005).

Al-Hajj et al., "Prospective identification of tumorigenic breast cancer cells," Proc. Natl. Acad. Sci. USA, 7:3983-88 (2003).

Altaner, "Glioblastoma and stem cells," Neoplasma, 55:369-374 (2008).

Beier et al., "CD133+ and CD133− glioblastoma-derived cancer stem cells show differential growth characteristics and molecular profiles," Cancer Res., 67:4010-15 (2007).

Bjerkvig et al., "Opinion: the origin of the cancer stem cell: current controversies and new insights," Nat. Rev. Cancer, 11:899-904 (2005).

Boman et al., "Cancer stem cells: a step toward the cure," J. Clin. Oncol., 26:2795-99 (2008).

Borbulevych et al., "Increased immunogenicity of an anchor-modified tumor-associated antigen is due to the enhanced stability of the peptide/MHC complex: implications for vaccine design," J. Immunol., 174:4812-20 (2005).

Borras et al., "Findings on T cell specificity revealed by synthetic combinatorial libraries," J. Immunol. Methods, 267:79-97 (2002).

Bowles, Jr. et al., "Long-term remission of malignant brain tumors after intracranial infection: a report of four cases," Neurosurgery, 44:636-642 (1999).

Brown et al., "Recognition and killing of brain tumor stem-like initiating cells by CD8+ cytolytic T cells," Cancer Res., 69:8886-93 (2009).

Candido et al., "Local administration of dendritic cells inhibits established breast tumor growth: implications for apoptosis-inducing agents," Cancer Res., 61:228-236 (2001).

Casey et al., "Heat shock protein derived from a non-autologous tumour can be used as an anti-tumour vaccine," Immunology, 110:105-111 (2003).

Castro et al., "Current and future strategies for the treatment of malignant brain tumors," Pharmacol. Ther., 98:71-108 (2003).

Chandler et al., "Long-term survival in patients with glioblastoma multiforme," Neurosurgery, 32:716-720 (1993).

Cho et al., "Recent advances of dendritic cells (DCs)-based immunotherapy for malignant gliomas," Cell Transplant., 18:977-983 (2009).

Curran et al., "Recursive partitioning analysis of prognostic factors in three radiation therapy oncology group malignant glioma trials," J. Natl. Cancer Inst., 85:704-710 (1993).

Dietz, "Engineering dendritic cell grafts for clinical trials in cellular immunotherapy of cancer: example of chronic myelogenous leukemia," Croatian Med. J., 42:428-435 (2001).

Ehtesham et al., "Intratumoral dendritic cell vaccination elicits potent tumoricidal immunity against malignant glioma in rats," J. Immunother., 26:107-116 (2003).

Ehtesham et al., "Recent progress in immunotherapy for malignant glioma: treatment strategies and results from clinical trials," Cancer Control, 11:192-207 (2004).

Falk et al., "Allele-specific motifs revealed by sequencing of self-peptides eluted from MHC molecules," Nature, 351:290-296 (1991).

(56) References Cited

OTHER PUBLICATIONS

Friedman et al., "Temozolomide and treatment of malignant glioma," Clin. Cancer Res., 6:2585-97 (2000).
Galli et al., "Isolation and characterization of tumorigenic, stem-like neural precursors from human glioblastoma," Cancer Res., 64:7011-21 (2004).
Gatza et al., "Tumor cell lysate-pulsed dendritic cells are more effective than TCR Id protein vaccines for active immunotherapy of T cell lymphoma," J. Immunol , 169:5227-35 (2002).
Geiger et al., "Vaccination of pediatric solid tumor patients with tumor lysate-pulsed dendritic cells can expand specific T cells and mediate tumor regression," Cancer Res., 61:8513-19 (2001).
Geschwind et al., "A genetic analysis of neural progenitor differentiation," Neuron, 2:325-39 (2001).
Ghods et al., "Spheres isolated from 9L gliosarcoma rat cell line possess chemoresistant and aggressive cancer stem-like cells," Stem Cells, 7:1645-53 (2007).
Gilboa et al., "Immunotherapy of cancer with dendritic-cell-based vaccines," Cancer Immunol. Immunother., 46:82-87 (1998).
Harada et al., "Melanoma-reactive CD8+ T cells recognize a novel tumor antigen expressed in a wide variety of tumor types," J. Immunother., 24:323-333 (2001).
Harizi et al., "Prostaglandin E2 modulates dendritic cell function via EP2 and EP4 receptor subtpes," J. Leukocyte Biol., 73:756-763 (2003).
Heimberger et al., "Bone marrow-derived dendritic cells pulsed with tumor homogenate induce immunity against syngeneic intracerebral glioma," J. Neuroimmunol., 103:16-25 (2000).
Hemmati et al., "Cancerous stem cells can arise from pediatric brain tumors," Proc. Natl. Acad. Sci. USA, 25:15178-83 (2003).
Hemmer et al., "Contribution of Individual Amino Acids Within MHC Molecule or Antigenic Peptide to TCR Ligand Potency," J. Immunol., 164:861-871 (2000).
Hirschmann-Jax et al., "A distinct 'side population' of cells with high drug efflux capacity in human tumor cells," Proc. Natl. Acad. Sci. USA, 39:14228-33 (2004).
Hori et al., "Neural progenitor cells lack immunogenecity and resist destruction as allografts," Stem Cells, 21:405-416 (2003).
Inoue et al., "Dendritic cells coinjected with tumor cells treated with an anticancer drug to induce tumor rejection," Surg. Today, 33:269-276 (2003).
Irvin et al., "T cells enhance stem-like properties and conditional malignancy in gliomas," PLoS One, 5(6):e10974 (2010).
Ji et al., "Glioma stem cell research for the development of immunotherapy," Neurosurg. Clin. N. Am., 21:159-66 (2010).
Kalinski et al., "Prostaglandin E2 induces the final maturation of IL-12 deficient CD1a+CD83+ dendritic cells: the levels of IL-12 are determined during the final dendritic cell maturation and are resistant to further modulation," J. Immunol, 161:2804-09 (1998).
Kikuchi et al., "Intratumoral injection of dendritic and irradiated glioma cells induces anti-tumor effects in a mouse brain tumor model," Cancer Immunol Immunother., 51:424-430 (2002).
Kikuchi et al., "Results of a phase I clinical trial of vaccination of glioma patients with fusions of dendritic and glioma cells," Cancer Immunol. Immumother., 50:337-344 (2001).
Knutson et al., "Technology evaluation: DCVax, Northwest Biotherapeutics," Curr. Opin. Mol. Ther., 4:403-407 (2002).
Kuby et al., Immunology, W. H. Freeman and Co., pp. 523-524 (1992).
La Rosa et al., "Enhanced immune activity of cytotoxic T-lymphocyte epitope analogs derived from positional scanning synthetic combinatorial libraries," Blood, 97:1776-86 (2001).
Lee et al., "Isolation of neural stem cells from the postnatal cerebellum," Nat. Neurosci., 6:723-729 (2005).
Lefranc, "Editorial: On the road to multi-modal and pluri-disciplinary treatment of glioblastomas," Acta Neurochir. (Wien), 151:109-112 (2009).
Liau et al., "Treatment of intracranial gliomas with bone marrow-derived dendritic cells pulsed with tumor antigens," J. Neurosurg., 90:1115-24 (1999).
Liu et al., "Cancer vaccines: a novel strategy to sensitize malignant glioma to chemotherapy," Expert Rev. Neurother., 7:1235-37 (2007).
Liu et al., "Analysis of gene expression and chemoresistance of CD133+ cancer stem cells in glioblastoma," Mol. Cancer, 5:67 (2006).
Liu et al., "Cell-mediated immunotherapy: a new approach to the treatment of malignant glioma," Cancer Control, 10:138-147 (2003).
Liu et al., "Chemoresistance of stem-like cells isolated from glioblastoma," Proc. Amer. Assoc. Cancer Res., 47:75, abstract #320 (2006).
Liu et al., "Small interference RNA modulation of IL-10 in human monocyte-derived dendritic cells enhances the Th1 response," Eur. J. Immunol., 34:1680-87 (2004).
Liu et al., "AIM-2: a novel tumor antigen is expressed and presented by human glioma cells," J. Immunother., 27:220-226 (2004).
Liu et al., "Cytotoxic T cell targeting of TRP-2 sensitizes human malignant glioma to chemotherapy," Oncogene, 24:5226-34 (2005).
Liu et al., "HER-2, gp100, and MAGE-1 are expressed in human glioblastoma and recognized by cytotoxic T cells," Cancer Res., 64:4980-86 (2004).
Liu et al., "Molecular and functional analysis of tyrosinase-related protein (TRP)-2 as a cytotoxic T lymphocyte target in patients with malignant glioma," J. Immunother., 26:301-312 (2003).
Liu et al., "Sensitization of malignant glioma to chemotherapy through dendritic cell vaccination," Expert Rev. Vaccines, 5:233-247 (2006).
Luptrawan et al., "Dendritic cell immunotherapy for malignant gliomas," Rev. Recent Clin. Trials, 3:10-21 (2008).
Lustgarten et al., "Identification of cross-reactive peptides using combinatorial libraries circumvents tolerance against Her-2/neu-immunodominant epitope," J. Immunol., 176:1796-1805 (2006).
Maitland et al., "Prostate cancer stem cells: a new target for therapy," J. Clin. Oncol., 26:2862-70 (2008).
Mammolenti et al., "Absence of major histocompatibility complex class I on neural stem cells does not permit natural killer cell killing and prevents recognition by alloreactive cytotoxic T lymphocytes in vitro," Stem Cells, 22:1101-10 (2004).
Mehta-Damani et al., "Generation of antigen-specific CD4+ T cell lines from naive precursors," Eur. J. Immunol., 5:1206-11 (1995).
Mehta-Damani et al., "Generation of antigen-specific CD8+ CTLs from naive precursors," J. Immunol., 153:996-1003 (1994).
Melcher et al., "Dendritic cells for the immunotherapy of cancer," Clin. Oncol., 14:185-192 (2002).
Merrick et al., "Autologous versus allogeneic peptide-pulsed dendritic cells for anti-tumour vaccination: expression of allogeneic MHC supports activation of antigen specific T cells, but impairs early naive cytotoxic priming and anti-tumour therapy," Cancer Immunol. Immunother., 57:897-906 (2008).
Mi et al., "Induced apoptosis supports spread of adenovirus vectors in tumors," Hum. Gene Ther., 12:1343-52 (2001).
Mizrak et al., "CD133: molecule of the moment," J. Pathol., 214:3-9 (2008).
NCBI GenBank Accession No. NM_006017 (Jul. 13, 2008).
Neuzil et al., "Tumour-initiating cells vs. cancer 'stem' cells and CD133: what's in the name?" Biochem. Biophys. Res. Commun., 355:855-859 (2007).
Nielsen et al., "Reliable prediction of T-cell epitopes using neural networks with novel sequence representations," Protein Sci., 12:1007-1017 (2003).
Nowak et al., "Synergy between chemotherapy and immunotherapy in the treatment of established murine solid tumors," Cancer Res., 63:4490-96 (2003).
O'Brien et al., "A human colon cancer cell capable of initiating tumour growth in immunodeficient mice," Nature, 7123:106-110 (2007).
Okada et al., "Bone marrow-derived dendritic cells pulsed with a tumor-specific peptide elicit effective anti-tumor immunity against intracranial neoplasms," Int. J. Cancer, 78:196-201 (1998).
Okada et al., "Autologous glioma cell vaccine admixed with interleukin-4 gene transfected fibroblasts in the treatment of recurrent glioblastoma: preliminary observations in a patient with a favorable response to therapy," J. Neurooncol., 64:13-20 (2003).

(56) References Cited

OTHER PUBLICATIONS

Okano et al., "Identification of a novel HLA-A*0201-restricted, cytotoxic T lymphocyte epitope in a human glioma-associated antigen, interleukin 13 receptor 12 chain," Clin. Cancer Res., 8:2851-55 (2002).
Osada et al., "Dendritic cells activate antitumor immunity for malignant intracranial germ cell tumor: a case report," Jpn. J. Clin. Oncol., 31:403-406 (2001).
Parkhurst et al., "Identification of a shared HLA-A*0201-restricted T-cell epitope from the melanoma antigen tyrosinase-related protein 2 (TRP2)," Cancer Res., 58:4895-4901 (1998).
Parkhurst et al., "Improved Induction of Melanoma-Reactive CTL with Peptides from the Melanoma Antigen gp100 Modified at HLA-A*0201-Binding Residues," J. Immunol., 157:2539-2548 (1996).
Parmiani et al., "Cancer immunotherapy with peptide-based vaccines: What have we achieved? Where are we going?" J. Natl. Cancer Inst., 94:805-818 (2002).
Parney et al., "Glioma immunology and immunotherapy," Neurosurgery, 46:778-792 (2000).
Pellegatta et al., "Dendritic cell vaccines for cancer stem cells," Methods Mol. Biol., 568:233-247 (2009).
Pellegatta et al., "Neurospheres enriched in cancer stem-like cells are highly effective in eliciting a dendritic cell-mediated immune response against malignant gliomas," Cancer Res., 66:10247-52 (2006).
Phuphanich et al., "Immune response correlation with progression-free survival in glioblastoma following dendritic cell immunotherapy (ICT-107)," J. Clin. Oncol., 28(15 suppl.):2097 (abstract) (2010).
Phuphanich et al., "Immune response correlation with progression-free survival in glioblastoma following dendritic cell immunotherapy (ICT-107)," poster presented at 2010 ASCO Annual Meeting, Jun. 4-8, 2010.
Pinilla et al., "Investigation of antigen-antibody interactions using a soluble, non-support-bound synthetic decapeptide library composed of four trillion ($4 \times 10^{12}$) sequences," Biochem. J., 301:847-853 (1994).
Pinilla et al., "Rapid identification of high affinity peptide ligands using positional scanning synthetic peptide combinatorial libraries," Biotechniques, 13:901-905 (1992).
Pirtskhalaishvili et al., "Cytokine-mediated protection of human dendritic cells from prostate cancer induced apoptosis is regulated by the Bcl-2 family of proteins," Br. J. Cancer, 83:506-513 (2000).
Pollack et al., "Exploitation of immune mechanisms in the treatment of central nervous system cancer," Semin. Pediatr. Neurol., 7:131-143 (2000).
Posnett et al., "A novel method for producing anti-peptide antibodies. Production of site-specific antibodies to the T cell antigen receptor beta-chain," J. Biol. Chem., 263:1719-25 (1988).
Reichardt et al., "Idiotype vaccination of multiple myeloma patients using monocyte-derived dendritic cells," Haematologica, 88:1139-49 (2003).
Reya et al., "Stem cells, cancer, and cancer stem cells," Nature, 6859:105-111 (2001).
Reynolds et al., "Generation of neurons and astrocytes from isolated cells of the adult mammalian central nervous system," Science, 5052:1707-10 (1992).
Reynolds et al, "A multipotent EGF-responsive striatal embryonic progenitor cell produces neurons and astrocytes," J. Neurosci., 11:4565-74 (1992).
Rissoan et al., "Reciprocal control of T helper cell and dendritic cell differentiation," Science, 283:1183-86 (1999).
Rosenberg et al., "Immunologic and therapeutic evaluation of a synthetic peptide vaccine for the treatment of patients with metastatic melanoma," Nat. Med., 4:321-327 (1998).
Sanai et al., "Neural stem cells and the origin of gliomas," N. Eng. J. Med., 8:811-822 (2005).
Shin et al., "Antitumor effect of intratumoral administration of dendritic cell combination with vincristine chemotherapy in a murine fibrosarcoma model," Histol. Histopathol., 18:435-447 (2003).
Singh et al., "Cancer stem cells in nervous tumors," Oncogene, 23:7267-73 (2004).
Singh et al., "Identification of a cancer stem cell in human brain tumors," Cancer Res., 63:5821-28 (2003).
Singh et al., "Identification of human brain tumor initiating cells," Nature, 7015:396-401 (2004).
Singh, "ImmunoCellular Therapeutics, Ltd.," presentation at 13th Annual Bio CEO & Investor Conference, Feb. 14, 2011.
Smith et al., "CD133/prominin-1 is a potential therapeutic target for antibody-drug conjugates in hepatocellular and gastric cancers," Br. J. Cancer, 99:100-109 (2008).
Söling et al., "Dendritic cell therapy of primary brain tumors," Mol. Med., 7:659-667 (2001).
Song et al., "Strategies to improve dendritic cell-based immunotherapy against cancer," Yonsei Med. J., 45(Suppl):48-52 (2004).
Steinbrink et al., "CD4+ and CD8+ anergic T cells induced by interleukin-10-treated human dendritic cells display antigen-specific suppressor activity," Blood, 99:2468-76 (2002).
Steinman, "Some interfaces of dendritic cell biology," APMIS, 111:675-697 (2003).
Stupp et al., "Recent Developments in the Management of Malignant Glioma," American Society of Clinical Oncology Educational Book, 779-788 (2003).
Takagi et al., "Anti-tumor effects of dendritic and tumor cell fusions are not dependent on expression of MHC class I and II by dendritic cells," Cancer Lett., 213:49-55 (2004).
Tanaka et al., "Intratumoral injection of dendritic cells after treatment of anticancer drugs induces tumor-specific antitumor effect in vivo," Int. J. Cancer, 101:265-269 (2002).
Tanaka et al., "Intratumoral injection of immature dendritic cells enhances antitumor effect of hyperthermia using magnetic nanoparticles," Int. J. Cancer, 116:624-633 (2005).
Tong et al., "Combined intratumoral injection of bone marrow-derived dendritic cells and systemic chemotherapy to treat pre-existing murine tumors," Cancer Res., 61:7530-35 (2001).
Tunici et al., "Brain tumor stem cells: new targets for clinical treatments?" Neurosurg. Focus, 4:E27 (2006).
Tunici et al., "Genetic alterations and in vivo tumorigenicity of neurospheres derived from an adult glioblastoma," Mol. Cancer, 3:25 (2004).
Wang et al., "An effective cancer vaccine modality: lentiviral modification of dendritic cells expressing multiple cancer-specific antigens," Vaccine, 24:3477-89 (2006).
Wei et al., "Dendritic cells expressing a combined PADRE/MUC4-derived polyepitope DNA vaccine induce multiple cytotoxic T-cell responses," Cancer Biother. Radiopharm., 23:121-128 (2008).
Weigel et al., "Dendritic cells pulsed or fused with AML cellular antigen provide comparable in vivo antitumor protective responses," Exp. Hematol., 34:1403-12 (2006).
Westphal et al., "Other experimental therapies for glioma," Recent Results Cancer Res., 171:155-164 (2009).
Wheeler et al., "Cellular immunity in the treatment of brain tumors," Clin. Neurosurg., 51:132-139 (2004).
Wheeler et al., "Clinical responsiveness of glioblastoma multiforme to chemotherapy after vaccination," Clin. Cancer Res., 10:5316-26 (2004).
Wheeler et al., "Thymic CD8+ T cell production strongly influences tumor antigen recognition and age-dependent glioma mortality," J. Immunol., 171:4927-33 (2003).
Wheeler et al., "Vaccination elicits correlated immune and clinical responses in glioblastoma multiforme patients," Cancer Res., 68:5955-64 (2008).
Wu et al., "Expression of MHC I and NK ligands on human CD133+ glioma cells: possible targets of immunotherapy," J. Neurooncol., 83:121-131 (2007).
Xu et al., "Antigen-specific T-cell response from dendritic cell vaccination using cancer stem-like cell-associated antigens," Stem Cells, 27:1734-40 (2009).
Yamazaki et al., "Direct expansion of functional CD25+ CD4+ regulatory T cells by antigen-processing dendritic cells," J. Exp. Med., 198:235-247 (2003).

(56) References Cited

OTHER PUBLICATIONS

Yang et al., "Modulation of major histocompatibility complex Class I molecules and major histocompatibility complex-bound immunogenic peptides induced by interferon-alpha and interferon-gamma treatment of human glioblastoma multiforme," J. Neurosurg., 100:310-319 (2004).
Yang et al., "Dendritic cells infected with a vaccinia vector carrying the human gp100 gene simultaneously present multiple specificities and elicit high-affinity T cells reactive to multiple epitopes and restricted by HLA-A2 and -A3," J Immunol., 164:4204-11 (2000).
Yasuda et al., "Dendritic cell-tumor cell hybrids enhance the induction of cytotoxic T lymphocytes against murine colon cancer: a comparative analysis of antigen loading methods for the vaccination of immunotherapeutic dendritic cells," Oncol. Rep., 16:1317-24 (2006).
Yin et al., "Expression and regulation of major histocompatibility complex on neural stem cells and their lineages," Stem Cells Dev., 17:53-65 (2008).
Yin et al., "AC133, a novel marker for human hematopoietic stem and progenitor cells," Blood, 90:5002-12 (1997).
Young et al., "Dendritic cells stimulate primary human cytolytic lymphocyte responses in the absence of CD4+ helper T cells," J. Exp. Med., 171:1315-32 (1990).
Yu et al., "AC133-2, a novel isoform of human AC133 stem cell antigen," J. Biol. Chem., 23:20711-16 (2002).
Yu et al., "Effective combination of chemotherapy and dendritic cell administration for the treatment of advanced-stage experimental breast cancer," Clin. Cancer Res., 9:285-294 (2003).
Yu et al., "Mahaley Clinical Research Award: chemosensitization of glioma through dendritic cell vaccination," Clin. Neurosurg., 53:345-351 (2006).
Yu et al., "Vaccination of malignant glioma patients with peptide-pulsed dendritic cells elicits systemic cytotoxicity and intracranial T-cell infiltration," Cancer Res., 61:842-847 (2001).
Yu et al., "Vaccination with tumor lysate-pulsed dendritic cells elicits antigen-specific, cytotoxic T-cells in patients with malignant glioma," Cancer Res., 64:4973-79 (2004).
Yuan et al., "Isolation of cancer stem cells from adult glioblastoma multiforme," Oncogene, 58:9392-9400 (2004).
Zabierowski et al., "Melanoma stem cells: the dark seed of melanoma," J. Clin. Oncol., 26:2890-94 (2008).
Zagzag et al., "Downregulation of major histocompatibility complex antigens in invading glioma cells: stealth invasion of the brain," Lab. Invest., 85:328-341 (2005).
Zeidler et al., "Tumor cell-derived prostaglandin E2 inhibits monocyte function by interfering with CCR5 and Mac-1," FASEB J., 14:661-668 (2000).
Zhang et al., "Antigenic profiling of glioma cells to generate allogeneic vaccines or dendritic cell-based therapeutics," Clin. Cancer Res., 13:566-575 (2007).
Zhu et al., "Insertion of the dibasic motif in the flanking region of a cryptic self-determinant leads to activation of the epitope-specific T cells," J. Immunol., 175:2252-60 (2005).
Zitvogel et al., "Therapy of murine tumors with tumor peptide-pulsed dendritic cells: dependence on T cells, B7 costimulation, and T helper cell-1 associated cytokines," J. Exp. Med., 183:87-97 (1996).
Zou, "Cancer initiating cells or cancer stem cells in the gastrointestinal tract and liver," J. Cell. Physiol., 217:598-604 (2008).
International Search Report and Written Opinion of International Application No. PCT/US2009/055759, mailed Jun. 28, 2010.
International Preliminary Report on Patentability of International Application No. PCT/US2009/055759, mailed Mar. 8, 2011.
Xu et al.; "Isolation of tumour stem-like cells from benign tumours"; *British Journal of Cancer*; (2009) 101, pp. 303-311.
Garcia-Hernandez et al., "Prostate Stem Cell Antigen Vaccination Induces a Long-term Protective Immune Response against Prostate Cancer in the Absence of Autoimmunity", Cancer Res., vol. 68, No. 3, (2008), pp. 861-869.

Haynes et al., "Molecular characterization of the B" regulatory subunit gene family of Arabidopsis protein phosphatase 2A", Euro J. Biochem., vol. 260, (1999), pp. 127-136.
Kimchi-Sarfaty et al., "A "Silent" Polymorphism in the MDR1 Gene Changes Substrate Specificity", Science, vol. 315, (2007), pp. 525-528 (Erratum, 1 page).
Weigmann et al., "Prominin, a novel microvilli-specific polytopic membrane protein of the apical surface of epithelial cells, is targeted to plasmalemmal protrusions of non-epithelial cells", Cell Biology, Proc. Natl. Acad. Sci. USA, vol. 94, (1997), pp. 12425-12430.
Yu et al. "CD133 as a Potential Target of Anti-Cancer Stem Cell Immunotherapy: Identification of an HLA-A*02 Restricted CD133 Epitope. Abstract", Journal of Immunotherapy, Nov.-Dec. 2008, p. 928.
Supplementary European Search Report for European Application No. 09812172.6, mailed May 4, 2012, 6 pages.
European Patent Office Communication for European Application No. 09812172.6, mailed May 23, 2012, 5 pages.
International Search Report and Written Opinion of International Application No. PCT/US2010/034082, mailed Feb. 22, 2011, 9 pages.
International Preliminary Report on Patentability for App. Ser. No. PCT/US2010/034082, mailed Nov. 17, 2011, 5 pages.
USPTO Non-Final Office Action in U.S. Appl. No. 12/776,200, mailed Apr. 18, 2012, 10 pages.
USPTO Non-Final Office Action in U.S. Appl. No. 12/776,200, mailed Aug. 7, 2012, 14 pages.
Abdel-Wahab et al., "Human dendritic cells, pulsed with either melanoma tumor cell lysates or the gp100 peptide(280-288), induce pairs of T-cell cultures with similar phenotype and lytic activity," Cell. Immunol., 186:63-74 (1998).
Akasaki et al., "Induction of a CD4+ T regulatory type 1 response by cyclooxygenase-2-overexpressing glioma," J. Immunol., 173:4352-59 (2004).
Akasaki et al., "T cell immunity in patients with malignant glioma: recent progress in dendritic cell-based immunotherapeutic approaches," Front. Biosci., 10:2908-21 (2005).
Bullock et al., "Antigen density presented by dendritic cells in vivo differentially affects the number and avidity of primary, memory, and recall CD8+ T cells," J. Immunol., 170:1822-29 (2003).
Carpentier et al., 2009, Neuron, 64: 79-92.
Castelli et al., "Novel HLA-Cw8-restricted T cell epitopes derived from tyrosinase-related protein-2 and gp100 melanoma antigens," J. Immunol., 162:1739-48 (1999).
Chen et al., "Identification of the MAGE-1 gene product by monoclonal and polyclonal antibodies," Proc. Natl. Acad. Sci. USA, 91:1004-08 (1994).
Czerniecki et al., "Targeting HER-2/neu in early breast cancer development using dendritic cells with staged interleukin-12 burst secretion," Cancer Res., 67:1842-52 (2007).
Debinsky, "Correspondence re: B. H. Joshi et al., Interleukin-13 Receptor I Chain: A Novel Tumor-associated Transmembrane Protein in Primary Explants of Human Malignant Gliomas. Cancer Res., 60: 1168-1172, 2000," Cancer Res., 61:5660 (2001).
Drukker et al., "Characterization of the expression of MHC proteins in human embryonic stem cells," Proc. Natl. Acad. Sci. USA, 99:9864-69 (2002).
Communication for Application No. EP 07843269.7, dated Feb. 2, 2011, 9 pages.
Gearhart, 1998, Science, 282: 1061-1062.
Haas et al., "Cycloxygenase-2 inhibition augments the efficacy of a cancer vaccine," Clin. Cancer Res., 12:214-222 (2006).
Hahn et al., "Short-term dietary administration of celecoxib enhances the efficacy of tumor lysate-pulsed dendritic cell vaccines in treating murine breast cancer," Int. J. Cancer, 118:2220-31 (2006).
International Preliminary Report on Patentability for App. Ser. No. PCT/US07/079846, mailed Apr. 9, 2009, 5 pages.
International Preliminary Report on Patentability for App. Ser. No. PCT/US07/079857, mailed Apr. 9, 2009, 5 pages.
International Search Report and Written Opinion of the International Searching Authority for PCT/US2007/79600, mailed on Mar. 27, 2008, 10 pages.

(56) References Cited

OTHER PUBLICATIONS

International Search Report and Written Opinion; PCT/US2014/16562; Jun. 3, 2014; 37 pp.
International Search Report and Written Opinion; PCT/US2014/16610; Jun. 5, 2014; 24 pp.
International Search Report of International Application No. PCT/US07/79846, mailed Jul. 14, 2008, 10 pages.
International Search Report of International Application No. PCT/US07/79857, mailed Apr. 8, 2008, 9 pages.
Joshi et al., "Interleukin-13 receptor I chain: a novel tumor-associated transmembrane protein in primary explants of human malignant gliomas," Cancer Res., 60:1168-72 (2000).
Khong et al., "Pre-existing immunity to tyrosinase-related protein (TRP)-2, a new TRP-2 isoform, and the NY-ESO-1 melanoma antigen in a patient with a dramatic response to immunotherapy," J. Immunol, 168:951-956 (2002).
Koch et al , "Immune-privileged embryonic Swiss mouse STO and STO cell-derived progenitor cells: major histocompatibility complex and cell differentiation antigen expression patterns resemble those of human embryonic stem cell lines," Immunology, 119:98-115 (2006).
Lemmel et al., "Differential quantitative analysis of MHC ligands by mass spectrometry using stable isotope labeling," Nat. Biotechnol., 22:450-454 (2004).
Li et al., "Human embryonic stem cells possess immune-privileged properties," Stem Cells, 22:448-456 (2004).
Lupetti et al., "Translation of a retained intron in tyrosinase-related protein (TRP) 2 mRNA generates a new cytotoxic T lymphocyte (CTL)-defined and shared human melanoma antigen not expressed in normal cells of the melanocytic lineage," J. Exp. Med., 188:1005-16 (1998).
Lynch et al., "Flt3 ligand induces tumor regression and antitumor immune responses in vivo," Nat. Med., 3:625-631 (1997).
Okada et al., "Induction of CD8+ T-Cell Responses Against Novel Glioma-Associated Antigen Peptides and Clinical Activity by Vaccinations With α-Type 1 Polarized Dendritic Cells and Polyinosinic-Polycytidylic Acid Stabilized by Lysine and Carboxymethylcellulose in Patients With Recurrent Malignant Glioma", J. Clin. Oncology, 29:330-336, (2011).
Ordonez et al.; "Value of Mesothelin Immunostaining in the Diagnosis of Mesothelioma"; Mod. Pathol., Mar. 2003; vol. 16, No. 3, pp. 192-197.
Pisarra et al., "Human melanocytes and melanomas express novel mRNA isoforms of the tyrosinase-related protein-2/DOPAchrome tautomerase gene: molecular and functional characterization," J. Invest. Dermatol., 115:48-56 (2000).
Salgaller et al., "Recognition of multiple epitopes in the human melanoma antigen gp100 by peripheral blood lymphocytes stimulated in vitro with synthetic peptides," Cancer Res., 55:4972-79 (1995).
Sette et al., "Epitope-based vaccines: an update on epitope identification, vaccine design and delivery", Current Opinion in Immunology, vol. 15, (2003), pp. 461-470.
Steele et al., "The polycomb group proteins, BMI-1 and EZH2, are tumour-associated antigens," Br. J. Cancer 95:1202-11 (2006).
Storkus et al., "Identification of human melanoma peptides recognized by class I restricted tumor infiltrating T lymphocytes," J. Immunol., 151:3719-27 (1993).
Tian et al., "Expression of immunoglobulin superfamily cell adhesion molecules on murine embryonic stem cells," Biol. Reprod., 57:561-568 (1997).
Tourdot et al., "A general strategy to enhance immunogenicity of low-affinity HLA-A2.1-associated peptides: implication in the identification of cryptic tumor epitopes", Eur. J. Immunol., vol. 30, (2000), pp. 3411-3421.
USPTO Final Office Action in U.S. Appl. No. 11/863,990, mailed May 12, 2011, 18 pages.
USPTO Final Office Action in U.S. Appl. No. 11/864,177, mailed May 13, 2011, 18 pages.
USPTO Non-Final Office Action in U.S. Appl. No. 11/863,990, mailed Aug. 26, 2010, 15 pages.
USPTO Non-Final Office Action in U.S. Appl. No. 11/864,177, mailed Aug. 26, 2010, 16 pages.
USPTO Final Office Action in U.S. Appl. No. 12/552,945, mailed Aug. 16, 2012, 13 pages.
USPTO Non-Final Office Action in U.S. Appl. No. 12/552,945, mailed Mar. 12, 2012, 20 pages.
Wang et al., "Identification of TRP-2 as a human tumor antigen recognized by cytotoxic T lymphocytes," J. Exp. Med., 184:2207-16 (1996).
Wu et al., "Embryonic stem cells and their differentiated derivatives have fragile immune privilege but still represent novel targets of immune attack," Stem Cells, 26:1939-50 (2008).
Xu et al., "Hedgehog signaling regulates brain tumor-initiating cell proliferation and portends shorter survival for patients with PTEN-coexpressing glioblastomas," Stem Cells, 26:3018-26 (2008).
Yamanaka et al; Vaccination of recurrent glioma patients with tumour lysate-pulsed dendritic cells elicits immune response: results of a clinical phase I/II trial; British Journal of Cancer (2003) 89, 1172-1179.
Zhou et al., "The ABC transporter Berp1/ABCG2 is expressed in a wide variety of stem cells and is a molecular determinant of the side-population phenotype," Nat. Med., 9:1028-34 (2001).
USPTO Final Office Action in U.S. Appl. No. 13/365,666, mailed Oct. 6, 2014, 14 pages.
USPTO Final Office action in U.S. Appl. No. 13/826,737, mailed Oct. 24, 2014, 33 pages.

* cited by examiner

```
Hs  ILSAFSVYV    (SEQ ID NO:1)
Pt  ILSEFSVYV    (SEQ ID NO:6)
Cf  KLSDFIGYI    (SEQ ID NO:7)
Ec  KLSNFMDYI    (SEQ ID NO:8)
Bt  TLSNFVRYI    (SEQ ID NO:9)
Rn  VLLQFSHYL    (SEQ ID NO:10)
Mm  MLLQVSHYL    (SEQ ID NO:11)
     *  .  *:
```

FIG. 9

CD133 EPITOPES

CROSS-REFERENCE TO RELATED APPLICATIONS

This application claims priority to U.S. Provisional Application Ser. No. 61/190,718, filed on Sep. 2, 2008, the entire contents of which are incorporated by reference herein.

TECHNICAL FIELD

This invention relates to methods and compositions for the treatment of cancers.

BACKGROUND

The cell surface marker CD133 (Prominin 1) is expressed by neural stem cells and has been used to select for brain cancer stem cells. In addition, CD133 positive cells are highly enriched for cancer stem cells in colon cancer, hepatocellular carcinoma, prostate cancer, multiple myeloma, and melanoma.

SUMMARY

This invention is based, at least in part, on the discovery of peptides of human CD133 that bind to human leukocyte antigens (HLA). These peptides can be used in immunotherapy of cancers. Accordingly, the invention includes at least compositions for cancer immunotherapy and methods for inducing immune responses in cancer patients against tumor antigens.

In one aspect, the invention features an immunogen that includes an isolated peptide of 800 amino acid residues or fewer (e.g., 700 amino acid residues or fewer, 600 amino acid residues or fewer, 500 amino acid residues or fewer, 400 amino acid residues or fewer, 300 amino acid residues or fewer, 200 amino acid residues or fewer, 150 amino acid residues or fewer, 100 amino acid residues or fewer, 80 amino acid residues or fewer, 60 amino acid residues or fewer, 50 amino acid residues or fewer, 40 amino acid residues or fewer, 30 amino acid residues or fewer, 20 amino acid residues or fewer, 15 amino acid residues or fewer, 14 amino acid residues or fewer, 13 amino acid residues or fewer, 12 amino acid residues or fewer, 11 amino acid residues or fewer, 10 amino acid residues or fewer, or 9 amino acid residues) that includes the amino sequence of any of SEQ ID NOs:1-13 with four or fewer (e.g., three or fewer, two or fewer, one or fewer, or zero) amino acid substitutions (e.g., conservative substitutions). In some embodiments, the immunogen includes a superagonist variant of any of SEQ ID NOs:1-11. In some embodiments, the immunogen includes one or more non-CD133 sequences.

In another aspect, the invention features compositions that include an immunogen described herein linked to an immunogenic carrier, e.g., a serum albumin, tetanus toxoid, keyhole limpet hemocyanin, dextran, an agonist of a Toll-like receptor (TLR), or a recombinant virus particle.

In other aspects, the invention features polynucleotides that include a nucleic acid sequence encoding an immunogen described herein. The polynucleotides can include an expression vector, e.g., a plasmid or a nonreplicative viral vector (e.g., vaccinia, fowlpox, Venezuelan equine encephalitis virus, adeno-associated virus, and adenovirus). In some embodiments the expression vector is a virus, e.g., an RNA or DNA virus.

In another aspect, the invention features compositions (e.g., pharmaceutical or vaccine compositions) that include an immunogen or polynucleotide described herein. The composition can further include an adjuvant (e.g., complete Freund's adjuvant, incomplete Freund's adjuvant, Montanide ISA-51, LAG-3, aluminum phosphate, aluminum hydroxide, alum, or saponin), a cytokine (e.g., Interleukin-1 (IL-1), IL-2, IL-7, IL-12, IL-13, IL-15, tumor necrosis factor (TNF), stem cell factor (SCF), or granulocyte monocyte colony stimulating factor (GM-CSF)), and/or an agonist of a Toll-like receptor (TLR) (e.g., an agonist of TLR-3, TLR-4, TLR-7, or TLR-9). The compositions can include a vehicle, e.g., a liposome (e.g., an emulsion, a foam, a micel, an insoluble monolayer, a liquid crystal, a phospholipid dispersion, or a lamellar layer), an immuno stimulating complex (ISCOM), or a slow-releasing particle.

In a further aspect, the invention features methods of immunization that include administering to a subject an immunogen, polynucleotide, or composition described herein in an amount effective to provoke an immune response.

In another aspect, the invention features methods for treating a subject with a cancer characterized by tumor cells expressing a class I MHC molecule or inhibiting or suppressing a cancer characterized by tumor cells expressing a class I MHC molecule in a subject. The methods include administering to the subject an immunogen, polynucleotide, or composition described herein in an amount effective to induce a CTL response directed against the tumor cells. In some embodiments, the methods include identifying the subject as having a cancer characterized by tumor cells expressing a class I MHC molecule.

In a further aspect, the invention features methods for treating a subject with a cancer characterized by tumor cells expressing HLA-A2 or for inhibiting or suppressing a cancer characterized by tumor cells expressing HLA-A2 in a subject. The methods include administering to the subject induced cytotoxic T lymphocyte (CTLs) in an amount sufficient to destroy the tumor cells through direct lysis or to effect the destruction of the tumor cells indirectly through the elaboration of cytokines, wherein the CTLs are induced by a process that includes inducing a CTL in vitro that is specific for the tumor cells by contacting a precursor CTL with an immunogen described herein under conditions that generate a CTL response to the tumor cells. In some embodiments, the methods include identifying the subject as having a cancer characterized by tumor cells expressing a class I MHC molecule or inhibiting or suppressing a cancer characterized by tumor cells expressing HLA-A2.

In another aspect, the invention features methods for treating a subject with a cancer characterized by tumor cells expressing any class I MHC molecule or inhibiting or suppressing a cancer characterized by tumor cells expressing a class I MHC molecule in a subject. The methods include administering to the subject induced cytotoxic T lymphocyte (CTLs) in an amount sufficient to destroy or inhibit the tumor cells through direct lysis or to effect the destruction or inhibition of the tumor cells indirectly through the elaboration of cytokines, wherein the CTLs are induced by a process comprising inducing a CTL in vitro that is specific for said tumor cells by contacting a precursor CTL with an immunogen described herein under conditions that generate a CTL response to the tumor cells. In some embodiments, the methods include identifying the subject as having a cancer characterized by tumor cells expressing a class I MHC molecule.

In a further aspect, the invention features methods for inducing a cytotoxic T lymphocyte (CTL) in vitro that is specific for a tumor cell expressing HLA-A2. The methods include contacting a precursor CTL with an immunogen described herein under conditions that generate a CTL response to the tumor cells.

In another aspect, the invention features methods for inducing a cytotoxic T lymphocyte (CTL) response in vitro that is specific for a tumor cell expressing HLA-A2. The methods include contacting a precursor CTL with a cell that includes a polynucleotide having a nucleic acid sequence encoding at least one polypeptide that includes an immunogen described herein.

In a further aspect, the invention features methods for treating a subject with a cancer characterized by tumor cells expressing HLA-A2 or inhibiting or suppressing a cancer characterized by tumor cells expressing HLA-A2 in a subject. The methods include administering CTLs induced by a method described herein in an amount effective to destroy the tumor cells through direct lysis or to effect the destruction of the tumor cells indirectly through the elaboration of cytokines. In some embodiments, the methods include identifying the subject as having a cancer characterized by tumor cells expressing HLA-A2.

The invention also features methods for treating, inhibiting, or suppressing a cancer in a subject. These methods include administering to the subject a composition including antigen-presenting cells (e.g., dendritic cells), wherein the antigen presenting cells present on their surface a peptide epitope comprising any of SEQ ID NOs:1-13 with four or fewer (e.g., three or fewer, two or fewer, one or fewer, or zero) amino acid substitutions (e.g., conservative substitutions) or a superagonist variant of any of SEQ ID NOs:1-11. In some embodiments, the antigen presenting cells (e.g., dendritic cells) acquire the peptide epitopes in vitro by exposure to synthetic peptides that include the peptide epitopes. In some embodiments, the methods include first identifying the subject as being in need of treatment, inhibition, or suppression of cancer.

In a further aspect, the invention features methods for preparing a cell vaccine for treating, inhibiting, or suppressing a cancer. The methods include obtaining bone marrow derived mononuclear cells from a patient, culturing the mononuclear cells in vitro under conditions in which mononuclear cells become adherent to a culture vessel; selecting a subset of the mononuclear cells comprising adherent cells; culturing the adherent cells in the presence of one or more cytokines under conditions in which the cells differentiate into antigen presenting cells; and culturing the antigen presenting cells in the presence of an immunogen described herein under conditions in which the cells present the peptides on major histocompatibility class I molecules, thereby preparing a cell vaccine.

In another aspect, the invention features kits that include one or more immunogens, polynucleotides, and/or compositions described herein.

In further aspects, the invention features an immunogen, polynucleotide, or composition described herein for use as a medicament; for use in therapy; for use in treating, inhibiting, or suppressing a tumor or cancer; or for use as a medicament for treating, inhibiting, or suppressing a tumor or cancer. In other aspects, the invention features the use of an immunogen, polynucleotide, or composition described herein for the manufacture of a medicament for treatment, inhibition, or suppression of a tumor or cancer.

A "superagonist" or "superantigen" peptide is a peptide that includes one or more mutations (e.g., one, two, or three amino acid changes, relative to a native (wild type) sequence) and that elicits an antigen-specific immunological response that is more potent than a response elicited against a peptide having a native sequence. For example, a superagonist peptide stimulates higher levels of IFN-γ release by antigen-specific T cells, as compared to T cells stimulated with the native peptide. The increase in levels of IFN-γ release stimulated by a superagonist peptide is higher than levels stimulated by a native peptide by a statistically significant amount. In some embodiments, a superagonist stimulates IFN-γ levels that are at least 5%, 10%, 25%, 50%, 100%, 200%, or 500% higher than the levels elicited by the native peptide.

Unless defined otherwise, technical and scientific terms used herein have the same meaning as commonly understood by one of ordinary skill in the art to which this invention belongs. Singleton et al., Dictionary of Microbiology and Molecular Biology 3rd ed., J. Wiley & Sons (New York, N.Y. 2001); March, Advanced Organic Chemistry Reactions, Mechanisms and Structure 5th ed., J. Wiley & Sons (New York, N.Y. 2001); Sambrook and Russel, Molecular Cloning: A Laboratory Manual 3rd ed., Cold Spring Harbor Laboratory Press (Cold Spring Harbor, N.Y. 2001); and Lutz et al., Handbook of Dendritic Cells: Biology, Diseases and Therapies, J. Wiley & Sons (New York, N.Y. 2006), provide one skilled in the art with a general guide to many of the terms used in the present application. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

BRIEF DESCRIPTION OF THE DRAWINGS

FIG. 1, CD133-405 tetramers.

FIG. 2, CD133-117 tetramers.
FIG. 3, CD133-301 tetramers.
FIG. 4, CD133-708 tetramers.
FIG. 5, CD133-804 tetramers.

FIG. 9 is an alignment of a human CD133 epitope (Hs; SEQ ID NO:1) and corresponding epitopes from chimpanzee (Pt, SEQ ID NO:6); dog (Cf, SEQ ID NO:7); horse (Ec, SEQ ID NO:8); cattle (Bt, SEQ ID NO:9); rat (Rn, SEQ ID NO:10); and mouse (Mm, SEQ ID NO:11). "*", residues are identical in all sequences; ":", conserved substitutions; ".", semi-conserved substitutions.

DETAILED DESCRIPTION

Figure 1:
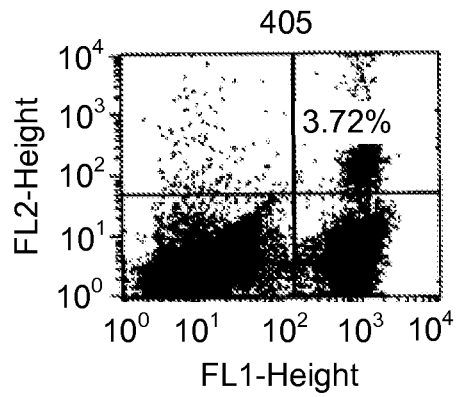
FIGS. 1 to 5 are a set of scatter plots of flow cytometry analysis of peptide-induced CTLs stained with phycoerythrin-conjugated HLA-A*0201/peptide tetramers (y-axis) and anti-human CD8-FITC mAbs (x-axis).
Figure 2:
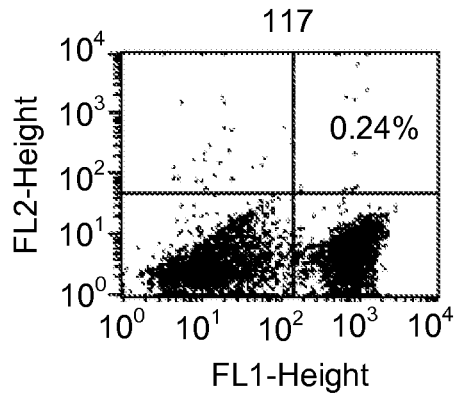
Figure 3:
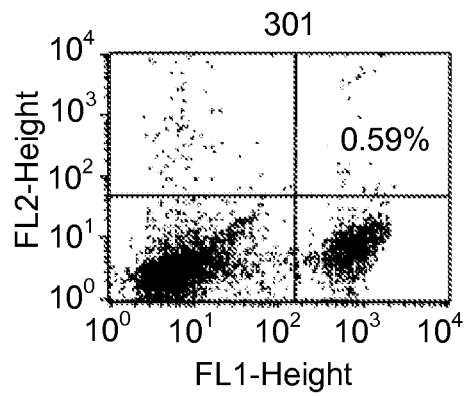
Figure 4:
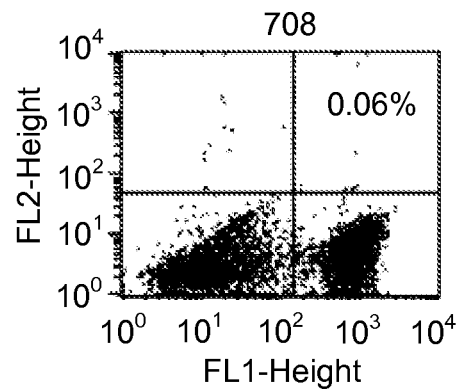
Figure 5:
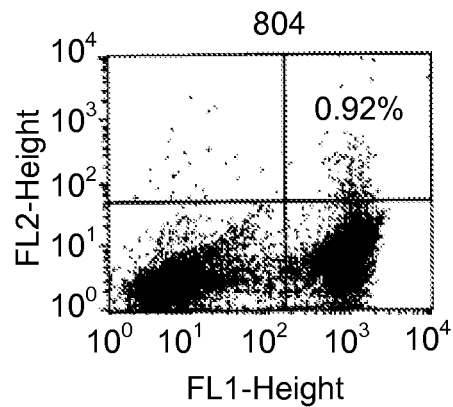

The present invention relates to immunogens and immunogenic compositions, and methods of use thereof, for the prevention, treatment, and/or diagnosis of cancers. Described herein are immunogens that include proteins or polypeptides whose amino acid sequences include one or more epitopic oligopeptides. In addition, the invention further relates to polynucleotides that can be used to stimulate a CTL response against cancers.

Described herein are specific oligopeptide sequences with amino acid sequences shown in SEQ ID NO:1-13, which represent epitopic peptides (i.e., immunogenic oligopeptide sequences) of at least about 9-10 amino acids in length.

CD133 is present in several human cancers (Mizrak et al., 2008, J. Pathol., 214:3-9; Neuzil et al., 2007, Biochem. Biophys. Res. Commun., 355:855-859), including brain cancer, colon cancer, hepatocellular carcinoma, prostate cancer, multiple myeloma, and melanoma.

An exemplary human CD133 sequence has the following amino acid sequence (SEQ ID NO:14). Epitope sequences identified herein (SEQ ID NO:1-5) are underlined.

(SEQ ID NO: 14)
MALVLGSLLLLGLCGNSFSGGQPSSTDAPKAWNYELPATNYETQDSHKA

GPIGILFELVHIFLYVVQPRDFPEDTLRKFLQKAYESKIDYDKPETVIL

GLKIVYYEAGIILCCVLG<u>LLFIILMPLV</u>GYFFCMCRCCNKCGGEMHQRQ

KENGPFLRKCFAISLLVICIIISIGIFYGFVANHQVRTRIKRSRKLADS

NFKDLRTLLNETPEQIKYILAQYNTTKDKAFTDLNSINSVLGGGILDRL

RPNIIPVLDEIKSMATAIKETKEALENMNSTLKSLHQQSTQLSSSLTSV

KTSLRS<u>SLNDPLCLV</u>HPSSETCNSIRLSLSQLNSNPELRQLPPVDAELD

NVNNVLRTDLDGLVQQGYQSLNDIPDRVQRQTTTVVAGIKRVLNSIGSD

IDNVTQRLPIQD<u>ILSAFSVYV</u>NNTESYIHRNLPTLEEYDSYWWLGGLVI

CSLLTLIVIFYYLGLLCGVCGYDRHATPTTRGCVSNTGGVFLMVGVGLS

FLFCWILMIIVVLTFVFGANVEKLICEPYTSKELFRVLDTPYLLNEDWE

YYLSGKLFNKSKMKLTFEQVYSDCKKNRGTYGTLHLQNSFNISEHLNIN

EHTGSISSELESLKVNLNIFLLGAAGRKNLQDFAACGIDRMNYDSYLAQ

TGKSPAGVNLLSFAYDLEAKANSLPPGNLRNSLKRDAQTIKTIHQQRVL

PIEQSLSTLYQSVKILQRTGN<u>GLLERVTRI</u>LASLDFAQNFITNNTSSVI

IEETKKYGRTIIGYFEHYLQWIEFSISEKVASCKPVATALDTAVDVFLC

SYIIDPLNLFWFGIGKATV<u>FLLPALIFAV</u>KLAKYYRRMDSEDVYDDVET

IPMKNMENGNNGYHKDHVYGIHNPVMTSPSQH

Counterparts of any of SEQ ID NOs:1-5 from other animals (e.g., mammals) can also be used as immunogens. Exemplary counterparts of SEQ ID NO:1 from other species include ILSEFSVYV (chimpanzee; SEQ ID NO:6); KLSDFIGYI (dog; SEQ ID NO:7); KLSNFMDYI (horse; SEQ ID NO:8); TLSNFVRYI (cattle; SEQ ID NO:9); VLLQFSHYL (rat; SEQ ID NO:10); and MLLQVSHYL (mouse; SEQ ID NO:11). An alignment of these sequences is presented in FIG. 9.

An exemplary CD133 epitope consensus sequence has the following formula: (I/K/T/V)-L-(S/L)-(A/E/N/D/Q)-F-(S/M/V/I)-(V/D/R/G/H)-Y-(V/I/L) (SEQ ID NO:12). Another exemplary CD133 epitope consensus sequence has the formula: (I/K/T/V/M)-L-(S/L)-(A/E/N/D/Q)-(F/V)-(S/M/V/I)-(V/D/R/G/H)-Y-(V/I/L) (SEQ ID NO:13).

The polypeptides forming the immunogens described herein have amino acid sequences that include SEQ ID NOs: 1-13 and variants thereof with four or fewer (e.g., three or fewer, two or fewer, one or fewer, or zero) amino acid substitutions (e.g., conservative substitutions).

Such polypeptides can be of any desired length so long as they have immunogenic activity in that they are able, under a given set of desirable conditions, to elicit in vitro or in vivo the activation of cytotoxic T lymphocytes (CTLs) (i.e., a CTL response) against a presentation of CD133 in vitro or in vivo by an antigen presenting cell (APC). Exemplary polypeptides include those of 800 amino acid residues or fewer (e.g., 700 amino acid residues or fewer, 600 amino acid residues or fewer, 500 amino acid residues or fewer, 400 amino acid residues or fewer, 300 amino acid residues or fewer, 200 amino acid residues or fewer, 150 amino acid residues or fewer, 100 amino acid residues or fewer, 80 amino acid residues or fewer, 60 amino acid residues or fewer, 50 amino acid residues or fewer, 40 amino acid residues or fewer, 30 amino acid residues or fewer, 20 amino acid residues or fewer, 15 amino acid residues or fewer, 14 amino acid residues or fewer, 13 amino acid residues or fewer, 12 amino acid residues or fewer, 11 amino acid residues or fewer, 10 amino acid residues or fewer, or 9 amino acid residues). The polypeptides forming the immunogens described herein can be naturally occurring or can be synthesized chemically. The polypeptides can include at least one of SEQ ID NOs:1-13.

Oligopeptides as disclosed herein may themselves be prepared by methods well known to those skilled in the art (Grant, G. A., Synthetic Peptides: A User's Guide, 1992, W. H. Freeman and Company, New York; Coligan, J. E. et al., Current Protocols in Protein Science, 1999, John Wiley & Sons, Inc., New York).

Besides the sequences of SEQ ID NO:1-13, the proteins and polypeptides forming the immunogens described herein can also include one or more other immunogenic amino acid stretches known to be associated with cancers, and which may stimulate a CTL response whereby the immunogenic peptides associate with HLA-A2, HLA-A1/A11, HLA supertypes, or any class I MHC (i.e., MHC-1) molecule.

The oligopeptides and polypeptides described herein can be derived by fractionation of naturally occurring proteins by methods such as protease treatment, or they can be produced by recombinant or synthetic methodologies that are well known and clear to the skilled artisan (See Ausubel, F. M. et al, Current Protocols in Molecular Biology, 1999, John Wiley & Sons, Inc., New York; Coligan, J. E. et al, Current Protocols in Protein Science, 1999, John Wiley & Sons, Inc., New York; Molecular Cloning: A Laboratory Manual, 1989, Cold Spring Harbor Laboratory Press, Cold Spring Harbor). The polypeptide can include a recombinant or synthetic polypeptide that includes at least one of SEQ ID NO:1-13, which sequences can also be present in multiple copies. Thus, oligopeptides and polypeptides disclosed herein can have one, two, three, or more such immunogenic peptides within the amino acid sequence of said oligopeptides and polypeptides, and said immunogenic peptides, or epitopes, can be the same or can be different, or can have any number of such sequences, wherein some of them are identical to each other in amino acid sequence while others within the same polypeptide sequence are different from each other and said epitopic sequences can occur in any order within said immunogenic polypeptide sequence. The location of such sequences within the sequence of a polypeptide forming an immunogen described herein can affect relative immunogenic activity. In addition, immunogens described herein can include more than one protein comprising the amino acid sequences disclosed herein. Such polypeptides can be part of a single composition or can themselves be covalently or non-covalently linked to each other.

The immunogenic peptides described herein can also be linked (e.g., covalently linked) directly to, or through a spacer or linker to: an immunogenic carrier such as serum albumin, tetanus toxoid, keyhole limpet hemocyanin, dextran, or a recombinant virus particle; a Toll-like receptor (TLR) agonist; an immunogenic peptide known to stimulate a T helper cell type immune response; a cytokine such as interferon gamma or GM-CSF; a targeting agent such as an antibody or receptor ligand; a stabilizing agent such as a lipid; or a conjugate of a plurality of epitopes to a branched lysine core structure, such as the so-called "multiple antigenic peptide" described in Posneft et al., 1988, J. Biol. Chem., 263:1719-25; a compound such as polyethylene glycol to increase the half life of the peptide; or additional amino acids such as a leader or secretory sequence, or a sequence employed for the purification of the mature sequence. Spacers and linkers typically include relatively small, neutral molecules, such as amino acids and which are substantially uncharged under physiological conditions. Such spacers are typically selected from the group of nonpolar or neutral polar amino acids, such as glycine, alanine, serine and other similar amino acids. Such optional spacers or linkers need not include the same residues and thus can be either homo- or hetero-oligomers. When present, such linkers will commonly be of length at least one or two, commonly 3, 4, 5, 6, and possibly as much as 10 or even up to 20 residues (in the case of amino acids). In addition, such linkers need not be composed of amino acids but any oligomeric structures will do as well so long as they provide the correct spacing so as to optimize the desired level of immunogenic activity of the immunogens described herein. The immunogen can therefore take any form that is capable of eliciting a CTL response.

In addition, the immunogenic peptides described herein can be part of an immunogenic structure via attachments other than conventional peptide bonds. Thus, any manner of attaching the peptides to an immunogen described herein, such as an immunogenic polypeptide, could provide an immunogenic structure. Thus, immunogens, such as proteins, oligopeptides and polypeptides, are structures that contain the peptides disclosed but such immunogenic peptides may not necessarily be attached thereto by the conventional means of using ordinary peptide bounds. The immunogens described herein simply contain such peptides as part of their makeup, but how such peptides are to be combined to form the final immunogen is left to the talent and imagination of the user and is in no way restricted or limited by the disclosure contained herein.

Modified Peptides

The peptides that are naturally processed and bound to a class I MHC molecule, and which are recognized by a tumor-specific CTL, are not necessarily the optimal peptides for stimulating a CTL response. See, for example, Parkhurst et al., 1996, J. Immunol., 157:2539-48; Rosenberg et al., 1998, Nat. Med., 4:321-32. Thus, there can be utility in modifying a peptide, such that it more readily or effectively induces a CTL response. Typically, peptides can be modified at two types of positions. The peptides can be modified at amino acid residues that are predicted to interact with the class I MHC molecule, in which case the goal is to create a peptide that has a higher affinity for the class I MHC molecule than does the original peptide. The peptides can also be modified at amino acid residues that are predicted to interact with the T cell receptor on the CTL, in which case the goal is to create a peptide that has a higher affinity for the T cell receptor than does the original peptide. Both of these types of modifications can result in a variant peptide that is related to an original peptide, but which is better able to induce a CTL response than is the original peptide. As used herein, the term "original peptide" means an oligopeptide with the amino acid sequence selected from SEQ ID NOs:1-11.

The original peptides disclosed herein can be modified by the substitution of one or more residues at different, possibly selective, sites within the peptide chain. Such substitutions can be of a conservative nature, for example, where one amino acid is replaced by an amino acid of similar structure and characteristics, such as where a hydrophobic amino acid is replaced by another hydrophobic amino acid. Even more conservative would be replacement of amino acids of the same or similar size and chemical nature, such as where leucine is replaced by isoleucine. In studies of sequence variations in families of naturally occurring homologous proteins, certain amino acid substitutions are more often tolerated than others, and these often show correlation with similarities in size, charge, polarity, and hydrophobicity between the original amino acid and its replacement, and such is the basis for defining "conservative substitutions."

Conservative substitutions are defined herein as exchanges within one of the following five groups: Group 1—small aliphatic, nonpolar or slightly polar residues (Ala, Ser, Thr, Pro, Gly); Group 2—polar, negatively charged residues and their amides (Asp, Asn, Glu, Gln); Group 3—polar, positively charged residues (His, Arg, Lys); Group 4—large, aliphatic, nonpolar residues (Met, Leu, Ile, Val, Cys); and Group 4—large, aromatic residues (Phe, Tyr, Trp).

Less conservative substitutions might involve the replacement of one amino acid by another that has similar characteristics, but is somewhat different in size, such as replacement of an alanine by an isoleucine residue. Highly nonconservative replacements might involve substituting an acidic amino acid for one that is polar, or even for one that is basic in character, or vice versa.

Such substitutions can also involve structures other than the common L-amino acids. Thus, D-amino acids might be substituted for the L-amino acids commonly found in the antigenic peptides described herein and yet still be encompassed by the present disclosure. In addition, amino acids possessing non-standard R groups (i.e., R groups other than those found in the 20 common amino acids of natural proteins) can also be used for substitution purposes to produce immunogens and immunogenic polypeptides.

Based on cytotoxicity assays, a substituted epitopic peptide is considered substantially identical to the reference peptide if it has at least 10% of the antigenic activity of the reference peptide as defined by the ability of the substituted peptide to reconstitute the epitope recognized by a CTL in comparison to the reference peptide. Thus, when comparing the lytic activity in the linear portion of the effector:target curves with equimolar concentrations of the reference and substituted peptides, the observed percent specific killing of the target cells incubated with the substituted peptide should be equal to that of the reference peptide at an effector:target ratio that is no greater than 10-fold above the reference peptide effector:target ratio at which the comparison is being made.

Thus, the epitopes described herein can be identical to naturally occurring tumor-associated or tumor-specific epitopes or can include epitopes that differ by no more than 4 residues from the reference peptide, as long as they have substantially identical antigenic activity.

It should be appreciated that an immunogen described herein can consist only of a peptide of SEQ ID NO:1-13, or include a peptide of SEQ ID NO:1-13, or include a plurality of peptides selected from SEQ ID NO:1-13, or include a polypeptide that itself includes one or more of the epitopic peptides of SEQ ID NO: 1-13. In some embodiments, an immunogen, composition, or kit described herein can further include a polypeptide, epitope, or other antigenic composition described in US 2007/0020297, US 2008/0206286, or US 2008/0311142, all of which are incorporated by reference herein.

Preparation of Immunogenic Peptides and Structures

The immunogenic peptides and polypeptides described herein can be prepared synthetically, by recombinant DNA technology, or they can be isolated from natural sources such as tumor cells expressing the original protein product.

The polypeptides and oligopeptides disclosed herein can be synthesized in solution or on a solid support in accordance with conventional techniques. Various automated peptide synthesizers are commercially available and can be used in accordance with known protocols. See, for example, Grant, G. A., Synthetic Peptides: A User's Guide, 1992, W. H. Freeman and Company, New York; Coligan, J. E. et al, Current Protocols in Protein Science, 1999, John Wiley & Sons, Inc., New York. Fragments of polypeptides described herein can also be synthesized as intermediates in the synthesis of a larger polypeptide.

Recombinant DNA technology can be employed wherein a nucleotide sequence that encodes an immunogenic peptide or polypeptide of interest is inserted into an expression vector, transformed or transfected into an appropriate host cell, and cultivated under conditions suitable for expression. These procedures are well known in the art to the skilled artisan, as described in Coligan, J. E. et al, Current Protocols in Immunology, 2006, John Wiley & Sons, Inc., New York; Ausubel, F. M. et al, Current Protocols in Molecular Biology, 1999, John Wiley & Sons, Inc., New York; Molecular Cloning: A Laboratory Manual, 1989, Cold Spring Harbor Laboratory Press, Cold Spring Harbor. Thus, recombinantly produced peptides or polypeptides can be used as the immunogens described herein.

The coding sequences for peptides of the length contemplated herein can also be synthesized on commercially available automated DNA synthesizers using protocols that are well know in the art. See for example, Grant, G. A., Synthetic Peptides: A User's Guide, 1992, W. H. Freeman and Company, New York; Coligan, J. E. et al, Current Protocols in Protein Science, 1999, John Wiley & Sons, Inc., New York. The coding sequences can also be modified such that a peptide or polypeptide will be produced that incorporates a desired amino acid substitution. The coding sequence can be provided with appropriate linkers, be ligated into suitable expression vectors that are commonly available in the art, and the resulting DNA or RNA molecule can be transformed or transfected into suitable hosts to produce the desired fusion protein. A number of such vectors and suitable host systems are available, and their selection is left to the skilled artisan. For expression of the fusion proteins, the coding sequence can provided with operably linked start and stop codons, promoter and terminator regions, and a replication system to provide an expression vector for expression in the desired host cell. For example, promoter sequences compatible with bacterial hosts can be provided in plasmids containing convenient restriction sites for insertion of the desired coding sequence. The resulting expression vectors are transformed into suitable bacterial hosts. Yeast, insect, and mammalian host cells can also be used, employing suitable vectors and control sequences.

Host cells can be genetically engineered (e.g., transduced, transformed, or transfected) with the vectors described herein which can be, for example, a cloning vector or an expression vector. The vector can be, for example, in the form of a plasmid, a viral particle, a phage, etc. The engineered host cells can be cultured in conventional nutrient media modified as appropriate for activating promoters, selecting transformants or amplifying the genes. The culture conditions, such as temperature, pH and the like, are those previously used with the host cell selected for expression, and will be apparent to the ordinarily skilled artisan.

The present invention also includes recombinant constructs comprising one or more of the sequences as broadly described above. The constructs include a vector, such as a plasmid or viral vector, into which a sequence described herein has been inserted, in a forward or reverse orientation. In a preferred aspect of this embodiment, the construct further includes regulatory sequences, including, for example, a promoter, operably linked to the sequence. Large numbers of suitable vectors and promoters are known to those of skill in the art, and are commercially available.

In a further embodiment, the present invention relates to host cells containing the above-described constructs. The host cell can be a higher eukaryotic cell, such as a mammalian cell, or a lower eukaryotic cell, such as a yeast cell, or the host cell can be a prokaryotic cell, such as a bacterial cell. Introduction of the construct into the host cell can be effected by calcium phosphate transfection, DEAE-Dextran mediated transfection, or electroporation (Ausubel, F. M. et al, Current Protocols in Molecular Biology, 1999, John Wiley & Sons, Inc., New York; Molecular Cloning: A Laboratory Manual, 1989, Cold Spring Harbor Laboratory Press, Cold Spring Harbor). Such cells can routinely be utilized for assaying CTL activity by having said genetically engineered, or recombinant, host cells express the immunogenic peptides described herein.

Various mammalian cell culture systems can also be employed to express recombinant protein. Examples of mammalian expression systems include the COS-7 lines of monkey kidney fibroblasts, described by Gluzman, 1981, Cell, 23:175, and other cell lines capable of expressing a compatible vector, for example, the C127, 3T3, CHO, HeLa and BHK cell lines. Mammalian expression vectors will include an origin of replication, a suitable promoter and enhancer, and also any necessary ribosome binding sites, polyadenylation site, splice donor and acceptor sites, transcriptional termination sequences, and 5' flanking non-transcribed sequences. DNA sequences derived from the SV40 splice, and polyadenylation sites can be used to provide the required nontranscribed genetic elements.

The polypeptides can be recovered and purified from recombinant cell cultures by methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Protein refolding steps can be used, as necessary, in completing configuration of the mature peptides and proteins. High performance liquid chromatography (HPLC) can be employed for final purification steps.

Antigen presenting cells that are to be used to stimulate a CTL response are typically incubated with a peptide of an optimal length, for example a nonapeptide, that allows for direct binding of the peptide to the class I MHC molecule without additional processing. Larger oligopeptides and polypeptides are generally ineffective in binding to class I MHC molecules as they are not efficiently processed into an appropriately sized peptide in the extracellular milieu. A variety of approaches are known in the art, however, that allow oligopeptides and polypeptides to be exogenously acquired by a cell, which then allows for their subsequent processing and presentation by a class I MHC molecule. Representative, but non-limiting examples of such approaches include electroporation of the molecules into the cell (Harding, 1992, Eur. J. Immunol., 22:1865-69), encapsulation of the molecules in liposomes that are fused to the cells of interest (Reddy et al., 1991, J. Immunol. Methods, 141:157-163), or osmotic shock in which the molecules are taken up via pinocytosis (Moore et al., 1988, Cell, 54:777-785). Thus, oligopeptides and polypeptides that include one or more of the peptides described herein can be provided to antigen presenting cells in such a fashion that they are delivered to the cytoplasm of the cell, and are subsequently processed to allow presentation of the peptides.

Antigen presenting cells suitable for stimulating an in vitro CTL response that is specific for one or more of the peptides described herein can also be prepared by introducing polynucleotide vectors encoding the sequences into the cells. These polynucleotides can be designed such that they express only a single peptide, multiple peptides, or even a plurality of peptides. A variety of approaches are known in the art that allow polynucleotides to be introduced and expressed in a cell, thus providing one or more peptides described herein to the class I MHC molecule binding pathway. Representative, but non-limiting examples of such approaches include the introduction of plasmid DNA through particle-mediated gene transfer or electroporation (Tuting et al., 1998, J. Immunol., 160:1139-47), or the transduction of cells with an adenovirus expressing the polynucleotide of interest (Perez-Diez et al., 1998, Cancer Res., 58:5305-09). Thus, oligonucleotides that code for one or more of the peptides described herein can be provided to antigen presenting cells in such a fashion that the peptides associate with class I MHC molecules and are presented on the surface of the antigen presenting cell, and consequently are available to stimulate a CTL response.

In certain embodiments, the methods described herein include a method for inducing a CTL response in vitro that is specific for a tumor cell expressing a molecule from A1, A2, or A3 supertypes (A11 is a member of the A3 supertype), whereby the method includes contacting a CTL precursor lymphocyte with an antigen presenting cell that has bound to an immunogen comprising one or more of the peptides disclosed herein.

In specific embodiments, the methods described herein include a method for inducing a CTL response in vitro that is specific for a tumor cell expressing a molecule from A1, A2, or A3 supertypes, whereby the method includes contacting a CTL precursor lymphocyte with an antigen presenting cell that has exogenously acquired an immunogenic oligopeptide or polypeptide that includes one or more of the peptides disclosed according to the invention.

A yet additional embodiment described herein is directed to a process for inducing a CTL response in vitro that is specific for a tumor cell expressing a molecule from A1, A2, or A3 supertypes, comprising contacting a CTL precursor lymphocyte with an antigen presenting cell that is expressing a polynucleotide coding for a polypeptide described herein, and wherein said polynucleotide is operably linked to a promoter.

A variety of techniques exist for assaying the activity of CTL. These techniques include the labeling of target cells with radionuclides such as $Na_2^{51}CrO_4$ or $^3H$-thymidine, and measuring the release or retention of the radionuclides from the target cells as an index of cell death. Such assays are well-known in the art. Alternatively, CTL are known to release a variety of cytokines when they are stimulated by an appropriate target cell, such as a tumor cell expressing the relevant class I MHC molecule and the corresponding peptide. Non-limiting examples of such cytokines include IFN-γ, TNF-α, and GM-CSF. Assays for these cytokines are well known in the art. Methodology for measuring both target cell death and cytokine release as a measure of CTL reactivity are given in Coligan, J. E. et al. (Current Protocols in Immunology, 1999, John Wiley & Sons, Inc., New York).

After expansion of the antigen-specific CTLs, the latter can then be transferred back into the patient, where they will destroy their specific target cell. The utility of such adoptive transfer is demonstrated in North et al. (199, Infect. Immun., 67:2010-12) and Riddell et al. (1992, Science, 257:238-241). In determining the number of cells to reinfuse, the skilled physician will be guided by the total number of cells available, the activity of the CTL as measured in vitro, and the condition of the patient. Typically, about $1 \times 10^6$ to about $1 \times 10^{12}$ (e.g., about $1 \times 10^8$ to about $1 \times 10^{11}$ or about $1 \times 10^9$ to about) $1 \times 10^{10}$) peptide-specific CTL are infused. Methods for reinfusing T cells into a patient are well known and exemplified in U.S. Pat. No. 4,844,893 to Honski, et al., and U.S. Pat. No. 4,690,915 to Rosenberg.

The peptide-specific CTL can be purified from the stimulator cells prior to infusion into the patient. For example, monoclonal antibodies directed toward the cell surface protein CD8, present on CTL, can be used in conjunction with a variety of isolation techniques such as antibody panning, flow cytometric sorting, and magnetic bead separation to purify the peptide-specific CTL away from any remaining non-peptide specific lymphocytes or from the stimulator cells. These methods are well known in the art. It should be appreciated that generation of peptide-specific CTL in this manner obviates the need for stimulating the CTL in the presence of tumor. Thus, there is no chance of inadvertently reintroducing tumor cells into the patient.

Thus, one embodiment of the present invention relates to a process for treating a subject who has cancer characterized by tumor cells expressing complexes of a molecule from A1, A2, or A3 supertypes, for example, HLA-A1, HLA-A2, or HLAA11, whereby CTLs produced in vitro according to the methods described herein are administered in an amount sufficient to destroy the tumor cells through direct lysis or to effect the destruction of the tumor cells indirectly through the elaboration of cytokines.

Another embodiment of the present invention is directed to a process for treating a subject with cancer characterized by tumor cells expressing any class I MHC molecule and an epitope of SEQ ID NO: 1-13, whereby the CTLs are produced in vitro and are specific for the epitope or original protein and are administered in an amount sufficient to destroy the tumor cells through direct lysis or to effect the destruction of the tumor cells indirectly through the elaboration of cytokines.

The ex vivo generated CTL can be used to identify and isolate the T cell receptor molecules specific for the peptide. The genes encoding the alpha and beta chains of the T cell receptor can be cloned into an expression vector system and transferred and expressed in naive T cells from peripheral blood, T cells from lymph nodes, or T lymphocyte progenitor cells from bone marrow. These T cells, which would then be expressing a peptide-specific T cell receptor, would then have anti-tumor reactivity and could be used in adoptive therapy of cancers.

Screening and Diagnostic Methods

In addition to their use for therapeutic or prophylactic purposes, the immunogenic peptides described herein are useful as screening and diagnostic agents. Thus, the immunogenic peptides described herein, together with modern techniques of gene screening, make it possible to screen patients for the presence of genes encoding such peptides on cells obtained by biopsy of tumors detected in such patients. The results of such screening can help determine the efficacy of proceeding with the regimen of treatment disclosed herein using the immunogens described herein.

Alternatively, the immunogenic peptides disclosed herein, as well as functionally similar homologs thereof, can be used to screen a sample for the presence of CTLs that specifically recognize the corresponding epitopes. The lymphocytes to be screened in this assay will normally be obtained from the peripheral blood, but lymphocytes can be obtained from other sources, including lymph nodes, spleen, tumors, and pleural fluid. The peptides described herein can then be used as a diagnostic tool to evaluate the efficacy of the immunotherapeutic treatments disclosed herein. Thus, the in vitro generation of CTL as described above would be used to determine if patients are likely to respond to the peptide in vivo. Similarly, the in vitro generation of CTL could be done with samples of lymphocytes obtained from the patient before and after treatment with the peptides. Successful generation of CTL in vivo should then be recognized by a correspondingly easier ability to generate peptide-specific CTL in vitro from lymphocytes obtained following treatment in comparison to those obtained before treatment.

The oligopeptides described herein, such as SEQ ID NOs: 1-13, can also be used to prepare multimers, which can be used, e.g., in conjunction with flow cytometry, to quantitate the frequency of peptide-specific CTL that are present in a sample of lymphocytes from an individual. For example, class I MHC molecules comprising peptides of SEQ ID NO:1-13, could be combined to form tetramers as exemplified in U.S. Pat. No. 5,635,363. Said tetramers can be used in monitoring the frequency of CTLs in the peripheral blood, lymph nodes, or tumor mass of an individual undergoing immunotherapy with the peptides, proteins, or polynucleotides described herein, and it would be expected that successful immunization would lead to an increase in the frequency of the peptide-specific CTL. A description of peptide tetramers and methods of using them can be found in Coligan, J. E. et al, Current Protocols in Immunology, 2006, John Wiley & Sons, Inc., New York.

Methods of Therapy

As stated above, a vaccine can include one or more of the polypeptides or active fragments thereof described herein, or a composition, or pool, of immunogenic peptides disclosed herein. When employing more than one polypeptide or active fragment, two or more polypeptides and/or active fragments can be used as a physical mixture or as a fusion of two or more polypeptides or active fragments. The fusion fragment or fusion polypeptide can be produced, for example, by recombinant techniques or by the use of appropriate linkers for fusing previously prepared polypeptides or active fragments.

The immunogenic molecules described herein, including vaccine compositions, can be utilized according to the methods described herein for purposes of inhibiting, suppressing, or treating diseases causing the expression of the immunogenic peptides disclosed herein, such as where the antigen is being expressed by tumor cells. As used in accordance with the present application, the term "inhibiting" relates to a process of prophylaxis in which an animal, especially a mammal, and most especially a human, is exposed to an immunogen described herein prior to the induction or onset of the disease process. This could be done where an individual has a genetic pedigree indicating a predisposition toward occurrence of the disease condition to be prevented. For example, this might be true of an individual whose ancestors show a predisposition toward certain types of cancer. Alternatively, the immunogen could be administered to the general population as is frequently done for infectious diseases.

Alternatively, the term "suppression" is often used to describe a condition wherein the disease process has already begun, but obvious symptoms of said condition have yet to be realized. Thus, the cells of an individual may have become cancerous, but no outside signs of the disease have yet been clinically recognized. In either case, the term prophylaxis can be applied to encompass both inhibition and suppression. Conversely, the term "treatment" is often utilized to mean the clinical application of agents to combat an already existing condition whose clinical presentation has already been realized in a patient. This would typically occur where an individual has already been diagnosed as having a tumor.

It is understood that the suitable dosage of an immunogen described herein will depend upon the age, sex, health, and weight of the recipient, the kind of concurrent treatment, if any, the frequency of treatment, and the nature of the effect desired. However, the most preferred dosage can be tailored to the individual subject, as determined by the researcher or clinician. The total dose required for any given treatment will commonly be determined with respect to a standard reference dose as set by a manufacturer, such as is commonly done with vaccines, such dose being administered either in a single treatment or in a series of doses, the success of which will depend on the production of a desired immunological result (i.e., successful production of a CTL-mediated response to the antigen, which response gives rise to the inhibition and/or treatment desired). Thus, the overall administration schedule must be considered in determining the success of a course of treatment and not whether a single dose, given in isolation, would or would not produce the desired immunologically therapeutic result or effect.

The therapeutically effective amount of a composition containing one or more of the immunogens described herein is an amount sufficient to induce an effective CTL response to inhibit or arrest disease progression. Thus, this dose will depend, among other things, on the identity of the immunogens used, the nature of the disease condition, the severity of the disease condition, the extent of any need to prevent such a condition where it has not already been detected, the manner of administration dictated by the situation requiring such administration, the weight and state of health of the individual receiving such administration, and the sound judgment of the clinician or researcher. Thus, for purposes of prophylactic or therapeutic administration, effective amounts would generally lie within the range of from 1.0 µg to about 5,000 µg of peptide for a 70 kg patient, followed by boosting dosages of from about 1.0 µg to about 1,000 µg of peptide pursuant to a boosting regimen over days, weeks or months, depending on the recipient's response and as necessitated by subsequent monitoring of CTL-mediated activity within the bloodstream. Of course, such dosages are to be considered only a general guide and, in a given situation, the actual dosage can exceed such suggested dosage regimens where the clinician believes that the recipient's condition warrants a more aggressive administration schedule. The efficacy of administering additional doses, and of increasing or decreasing the interval, can be re-evaluated on a continuing basis, in view of the recipient's immunocompetence (for example, the level of CTL activity with respect to tumor-associated or tumor-specific antigens).

For such purposes, the immunogenic compositions described herein can be used against a disease condition such as cancer by administration to an individual by a variety of routes. The compositions can be administered parenterally or orally, and, if parenterally, either systemically or topically. Parenteral routes include subcutaneous, intravenous, intradermal, intramuscular, intraperitoneal, intranasal, transdermal, or buccal routes. One or more such routes can be employed. Parenteral administration can be, for example, by bolus injection or by gradual perfusion over time.

Typically, vaccines are prepared as injectables, in the form of aqueous solutions or suspensions. Vaccines in an oil base are also well known such as for inhaling. Solid forms that are dissolved or suspended prior to use can also be formulated. Pharmaceutical carriers, diluents and excipients are generally added that are compatible with the active ingredients and acceptable for pharmaceutical use. Examples of such carriers include, but are not limited to, water, saline solutions, dextrose, or glycerol. Combinations of carriers can also be used. These compositions can be sterilized by conventional, well known sterilization techniques including sterile filtration. The resulting solutions can be packaged for use as is, or the aqueous solutions can be lyophilized, the lyophilized preparation being combined with sterile water before administration. Vaccine compositions can further incorporate additional substances to stabilize pH, or to function as adjuvants, wetting agents, or emulsifying agents, which can serve to improve the effectiveness of the vaccine.

The concentration of the CTL stimulatory peptides described herein in pharmaceutical formulations are subject to wide variation, including anywhere from less than 0.01% by weight to as much as 50% or more. Factors such as volume and viscosity of the resulting composition must also be considered. The solvents, or diluents, used for such compositions include water, dimethylsulfoxide, PBS (phosphate buffered saline), or saline itself, or other possible carriers or excipients.

The immunogens described herein can also be contained in artificially created structures such as liposomes, ISCOMS, slow-releasing particles, and other vehicles which increase the immunogenicity and/or half-life of the peptides or polypeptides in serum. Liposomes include emulsions, foams, micelles, insoluble monolayers, liquid crystals, phospholipid dispersions, lamellar layers and the like. Liposomes for use in the methods and compositions described herein are formed from standard vesicle-forming lipids which generally include neutral and negatively charged phospholipids and a sterol, such as cholesterol. The selection of lipids is generally determined by considerations such as liposome size and stability in the blood. Various methods are available for preparing liposomes as reviewed, for example, by (Coligan, J. E. et al, Current Protocols in Protein Science, 1999, John Wiley & Sons, Inc., New York) and see also U.S. Pat. Nos. 4,235,871, 4,501,728, 4,837,028, and 5,019,369. Liposomes containing the peptides or polypeptides described herein can be directed to the site of lymphoid cells where the liposomes then deliver the selected immunogens directly to antigen presenting cells. Targeting can be achieved by incorporating additional molecules such as proteins or polysaccharides into the outer membranes of said structures, thus resulting in the delivery of the structures to particular areas of the body, or to particular cells within a given organ or tissue. Such targeting molecules can include a molecule that binds to receptor on antigen presenting cells. For example an antibody that binds to CD80 could be used to direct liposomes to dendritic cells.

The immunogens described herein can also be administered as solid compositions. Conventional nontoxic solid carriers including pharmaceutical grades of mannitol, lactose, starch, magnesium, cellulose, glucose, sucrose, sodium saccharin, and the like. Such solid compositions will often be administered orally, whereby a pharmaceutically acceptable nontoxic composition is formed by incorporating the peptides and polypeptides described herein with any of the carriers listed above. Generally, such compositions will contain 10-95% active ingredient, and more preferably 25-75% active ingredient.

Aerosol administration is also an alternative, requiring only that the immunogens be properly dispersed within the aerosol propellant. Typical percentages of the peptides or polypeptides described herein are 0.01%-20% by weight, e.g., 1%-10%. The use of a surfactant to properly disperse the immunogen may be required. Representative surfactants include the esters or partial esters of fatty acids containing from 6 to 22 carbon atoms, such as caproic, octanoic, lauric, palmitic, stearic, linoleic, linolenic, olesteric and oleic acids with an aliphatic polyhydric alcohol or its cyclic anhydride. Mixed esters, such as mixed or natural glycerides can be employed. The surfactant can constitute 0.1-20% by weight of the composition, e.g., 0.25-5%. Typical propellants for such administration can include esters and similar chemicals but are by no means limited to these. A carrier, such as lecithin, can also be included for intranasal delivery.

The peptides and polypeptides described herein can also be delivered with an adjuvant. Adjuvants include, but are not limited to, Toll-like receptor (TLR) agonists, Bacillus Calmette Guerin (BCG), complete or incomplete Freund's adjuvant, a cytosine guanine oligodeoxynucleotide (CpG-ODN), Montanide ISA-51, Activation Gene-3 (LAG-3), aluminum phosphate, aluminum hydroxide, alum, and saponin. Adjuvant effects can also be obtained by administering one or more cytokines along with the immunogens described herein. These cytokines include, but are not limited to IL-1, IL-2, IL-7, IL-12, IL-13, IL-15, IL-18, and GM-CSF. Exemplary TLR agonists are described in Ghosh et al., 2006, Cell. Immunol., 243:48-57 and Lippincott's Illustrated Reviews: Immunology, Lippincott Williams & Wilkins; (Jul. 1, 2007), ISBN-10: 0781795435, Page 17.

The peptides and polypeptides described herein can also be added to professional antigen presenting cells such as dendritic cells that have been prepared ex vivo. For example, the dendritic cells can be prepared from CD34 positive stem cells from the bone marrow, or they can be prepared from CD14 positive monocytes obtained from the peripheral blood. The dendritic cells are generated ex vivo using cytokines such as GM-CSF, IL-3, IL-4, TNF, and SCF. The cultured DCs are then pulsed with peptides at various concentrations using standard methods that are well known in the art. The peptide-pulsed dendritic cells can then be administered intravenously, subcutaneously, or intradermally, and the immunization can also include cytokines such as IL-2 or IL-12.

An antigen presenting cell (APC)-based cancer vaccine can be delivered to a patient or test animal by any suitable delivery route, which can include injection, infusion, inoculation, direct surgical delivery, or any combination thereof. In some embodiments, the cancer vaccine is administered to a human in the deltoid region or axillary region. For example, the vaccine is administered into the axillary region as an intradermal injection. In other embodiments, the vaccine is administered intravenously.

An appropriate carrier for administering APCs can be selected by one of skill in the art by routine techniques. For example, the pharmaceutical carrier can be a buffered saline solution, e.g., cell culture media, and can include DMSO for preserving cell viability.

The quantity of APCs appropriate for administration to a patient as a cancer vaccine can be based upon a variety of factors, as can the formulation of the vaccine itself. Some of these factors include the physical characteristics of the patient (e.g., age, weight, and sex), the physical characteristics of the tumor (e.g., location, size, rate of growth, and accessibility), and the extent to which other therapeutic methodologies (e.g., chemotherapy, and beam radiation therapy) are being implemented in connection with an overall treatment regimen. Notwithstanding the variety of factors one should consider in implementing the methods described herein to treat a disease condition, a mammal can be administered with from about $10^5$ to about $10^8$ APCs (e.g., $10^7$ APCs) in from about 0.05 mL to about 2 mL solution (e.g., saline) in a single administration. Additional administrations can be carried out, depending upon the above-described and other factors, such as the severity of tumor pathology. In one embodiment, from about one to about five administrations of about $10^6$ APCs is performed at two-week intervals.

APC vaccination can be accompanied by other treatments. For example, a patient receiving APC vaccination can also be receiving chemotherapy, radiation, and/or surgical therapy concurrently. Methods of treating cancer using APC vaccination in conjunction with chemotherapy are described in Wheeler et al., U.S. Pat. Pub. No. 2007/0020297. In some embodiments, a patient receiving DC vaccination has already received chemotherapy, radiation, and/or surgical treatment for the cancer. In one embodiment, a patient receiving DC vaccination is treated with a COX-2 inhibitor, as described in Yu and Akasaki, WO 2005/037995 and US 2008/0199484.

The present invention is also directed to a vaccine in which an immunogen described herein is delivered or administered in the form of a polynucleotide encoding the a polypeptide or active fragment as disclosed herein, whereby the peptide or polypeptide or active fragment is produced in vivo. The polynucleotide can be included in a suitable expression vector and combined with a pharmaceutically acceptable carrier. For example, the peptides or polypeptides could be expressed in plasmid DNA and nonreplicative viral vectors such as vaccinia, fowlpox, Venezuelan equine encephalitis virus, adenovirus, or other RNA or DNA viruses. These examples are meant to be illustrative only and should not be viewed as limiting. A wide variety of other vectors are available and are apparent to those skilled in the art from the description given herein. In this approach, a portion of the nucleotide sequence of the viral vector is engineered to express the peptides or polypeptides described herein. Vaccinia vectors and methods useful in immunization protocols are described in U.S. Pat. No. 4,722,848, the disclosure of which is incorporated herein by reference in its entirety.

Regardless of the nature of the composition given, additional therapeutic agents can also accompany the immunogens described herein. Thus, for purposes of treating tumors, compositions containing the immunogens disclosed herein can, in addition, contain other antitumor pharmaceuticals. The use of such compositions with multiple active ingredients is left to the discretion of the clinician.

In addition, the immunogens described herein can be used to stimulate the production of antibodies for use in passive immunotherapy, for use as diagnostic reagents, and for use as reagents in other processes such as affinity chromatography.

The present invention also relates to antibodies that react with immunogens, such as a polypeptide comprising one or more of the epitopic peptides of SEQ ID NO: 1-13 as described herein. Active fragments of such antibodies are also specifically contemplated. Such antibodies, and active fragments of such antibodies, for example, and Fab structure, can react with, including where it is highly selective or specific for, an immunogenic structure comprising 2, 3, 4 or more of the epitopic peptides described herein.

With the advent of methods of molecular biology and recombinant technology, it is now possible for the artisan of ordinary skill to produce antibody molecules by recombinant means and thereby generate gene sequences that code for specific amino acid sequences found in the polypeptide structure of the antibodies. Such antibodies can be produced by either cloning the gene sequences encoding the polypeptide chains of said antibodies or by direct synthesis of said polypeptide chains, with in vitro assembly of the synthesized chains to form active tetrameric ($H_2L_2$) structures with affinity for specific epitopes and antigenic determinants. This has permitted the ready production of antibodies having sequences characteristic of neutralizing antibodies from different species and sources.

Regardless of the source of the antibodies or nanobodies, or how the artisan of ordinary skill chooses to produce such antibodies or nanobodies, including recombinantly constructed or synthesized, in vitro or in vivo, by using transgenic animals, such as cows, goats and sheep, or by using cell cultures in bioreactors, or by direct chemical synthesis employing no living organisms at any stage of the process, all antibodies and nanobodies have regions capable of interacting with a structurally complementary antigenic target. The regions interacting with the target are referred to as "variable" or "V" regions and are characterized by differences in amino acid sequence from antibodies of different antigenic specificity.

The antibodies can also be wholly synthetic, wherein the polypeptide chains of the antibodies are synthesized and, possibly, optimized for binding to the polypeptides disclosed herein as being receptors. Such antibodies can be chimeric or humanized antibodies and can be fully tetrameric in structure, or can be dimeric and include only a single heavy and a single light chain. Such antibodies can also include fragments, such as Fab and F(ab')$_2$ fragments, capable of reacting with and binding to any of the polypeptides disclosed herein as being receptors.

A further embodiment of the present invention relates to a method for inducing a CTL response in a subject comprising administering to subjects that express HLA A1, A2 or A3 supertype antigens an effective (i.e., CTL-stimulating) amount of an immunogen described herein, e.g., an amount sufficient to induce a CTL response to tumor cells expressing at least HLA-A1 or HLA-A2, as the case may be, thereby eliciting a cellular response against said tumor cells.

A still further embodiment of the present invention relates to a method for inducing a CTL response in a subject, wherein the immunogen is in the form of a polynucleotide. In one non-limiting example, the method includes administering to subjects that express HLA-A2 at least one CTL epitope, wherein said epitope or epitopes are selected from a group comprising the peptides described herein, and are coded within a polynucleotide sequence that does not include the entire protein coding region, in an amount sufficient to induce a CTL response to tumor cells expressing HLA-A2.

The peptides and immunogens disclosed herein can also include mutations (e.g., internal mutations) that render them "superantigens" or "superagonists" for T cell stimulation.

Superantigen peptides can be generated by screening T cells with a positional scanning synthetic peptide combinatorial library (PS-CSL) as described in Pinilla et al., 1992, Biotechniques, 13:901-5; Borras et al., 2002, J. Immunol. Methods, 267:79-97; US 2004/0072246; and Lustgarten et al., 2006, J. Immun., 176:1796-1805. When a native T cell epitope is known, approximately 25% of the identified epitope mimics are found to be superagonists. Superagonist epitope mimics that are 3 orders of magnitude more effective than the native ligand have been reported (Hemmer et al., 2000, J. Immunol., 164: 861-871; La Rosa et al., 2001, Blood, 97:1776-86).

Positional scanning synthetic combinatorial libraries (PS-SCLs) representing trillions of peptides of different lengths can be used as unbiased sources of peptide antigens in T cell activation assays for the identification of T cell epitopes. PS-SCL (Pinilla et al., 1992, Biotechniques, 13:901-905) are composed of systematically arranged mixtures. In the case of a single position defined PS-SCL, each compound present in a given mixture has a common individual amino acid at a given position, while the remaining positions are composed of mixtures of all 19 natural L-amino acids (cysteine omitted). The screening data of a given PS-SCL permits the identification of key residues at each position of the peptide. It is important to note, however, that the activity found for a mixture is due to the presence of specific active peptide(s) within the mixture, and not to the individual amino acids as separate entities. The combination of all amino acids defined in the most active mixtures leads to the active individual compounds.

The antigen-specific cellular immune responses of vaccinated subjects can be monitored by a number of different assays, such as tetramer assays, ELISPOT, and quantitative PCR. The following sections provide examples of protocols for detecting responses with these techniques. Additional methods and protocols are available. See e.g., Current Protocols in Immunology, Coligan, J. et al., Eds., (John Wiley & Sons, Inc.; New York, N.Y.).

Tetramers comprised of recombinant MHC molecules complexed with peptide can be used to identify populations of antigen-specific T cells. To detect T cells specific for antigens such as CD133, fluorochrome labeled specific peptide tetramer complexes (e.g., phycoerythrin (PE)-tHLA) containing peptides from these antigens are synthesized and provided by Beckman Coulter (San Diego, Calif.). Specific CTL clone CD8 cells are resuspended at $10^5$ cells/50 μl FACS buffer (phosphate buffer plus 1% inactivated FCS buffer). Cells are incubated with 1 μl tHLA for 30 minutes at room temperature and incubation is continued for 30 minutes at 4° C. with 10 μl anti-CD8 mAb (Becton Dickinson, San Jose, Calif.). Cells are washed twice in 2 ml cold FACS buffer before analysis by FACS (Becton Dickinson).

ELISPOT assays can be used to detect cytokine secreting cells, e.g., to determine whether cells in a vaccinated patient secrete cytokine in response to antigen, thereby demonstrating whether antigen-specific responses have been elicited. ELISPOT assay kits are supplied from R & D Systems (Minneapolis, Minn.) and performed as described by the manufacturer's instructions. Responder (R) $1\times10^5$ patients' PBMC cells from before and after vaccination are plated in 96-well plates with nitrocellulose membrane inserts coated with capture Ab. Stimulator (S) cells (TAP-deficient T2 cells pulsed with antigen) are added at the R:S ratio of 1:1. After a 24-hour incubation, cells are removed by washing the plates 4 times. The detection Ab is added to each well. The plates are incubated at 4° C. overnight and the washing steps will be repeated. After a 2-hour incubation with streptavidin-AP, the plates are washed. Aliquots (100 μl) of BCIP/NBT chromogen are added to each well to develop the spots. The reaction is stopped after 60 min by washing with water. The spots are scanned and counted with computer-assisted image analysis (Cellular Technology Ltd, Cleveland, Ohio). When experimental values are significantly different from the mean number of spots against non-pulsed T2 cells (background values), as determined by a two-tailed Wilcoxon rank sum test, the background values are subtracted from the experimental values.

Quantitative PCR is another means for evaluating immune responses. To examine IFN-γ production in patients by quantitative PCR, cryopreserved PBMCs from patients' pre-vaccination and post-vaccinations samples and autologous dendritic cells are thawed in RPMI DC culture medium with 10% patient serum, washed and counted. PBMC are plated at $3\times10^6$ PBMCs in 2 ml of medium in 24-well plate; dendritic cells are plated at $1\times10^6$/ml and are pulsed 24 hour with 10 μg/ml tumor peptide in 2 ml in each well in 24 well plate. Dendritic cells are collected, washed, and counted, and diluted to $1\times10^6$/ml, and $3\times10^5$ (i.e., 300 μl solution) added to wells with PBMC (DC:PBMC=1:10). 2.3 μl IL-2 (300 IU/mL) is added every 3-4 days, and the cells are harvested between day 10 and day 13 after initiation of the culture. The harvested cells are then stimulated with tumor cells or autologous PBMC pulsed with 10 μg/ml tumor peptide for 4 hours at 37° C. On days 11-13, cultures are harvested, washed twice, then divided into four different wells, two wells using for control (without target); and another two wells CTL co-cultured with tumor cells (1:1) if tumor cells are available. If tumor cells are not available, 10 μg/ml tumor lysate is added to CTL. After 4 hours of stimulation, the cells are collected, RNA extracted, and IFN-γ and CD8 mRNA expression evaluated with a thermocycler/fluorescence camera system. PCR amplification efficiency follows natural log progression, with linear regression analyses demonstrating correlation coefficients in excess of 0.99. Based on empirical analysis, a one-cycle difference is interpreted to be a two-fold difference in mRNA quantity, and CD8-normalized IFN-γ quantities are determined. An increase of >1.5-fold in post-vaccine relative to pre-vaccine IFN-γ is the established standard for positive type I vaccine responsiveness.

The following protocol can be used to produce antigen specific CTL in vitro from patient-derived PBMC. To generate dendritic cells, the plastic adherent cells from PBMCs are cultured in AIM-V medium supplemented with recombinant human GM-CSF and recombinant human IL-4 at 37° C. in a humidified $CO_2$ (5%) incubator. Six days later, the immature dendritic cells in the cultures are stimulated with recombinant human TNF-α for maturation. Mature dendritic cells are then harvested on day 8, resuspended in PBS at $1\times10^6$ per mL with peptide (2 μg/mL), and incubated for 2 hours at 37° C. Autologous CD8+ T cells are enriched from PBMCs using magnetic microbeads (Miltenyi Biotech, Auburn, Calif.). CD8+ T cells ($2\times10^6$ per well) are co-cultured with $2\times10^5$ per well peptide-pulsed dendritic cells in 2 mL/well of AIM-V medium supplemented with 5% human AB serum and 10 units/mL rhIL-7 (Cell Sciences) in each well of 24-well tissue culture plates. About 20 U/ml of IL-2 is added 24 h later at regular intervals, 2 days after each restimulation. On day 7, lymphocytes are restimulated with autologous dendritic cells pulsed with peptide in AIM-V medium supplemented with 5% human AB serum, rhIL-2, and rhIL-7 (10 units/mL each). About 20 U/ml of IL-2 is added 24 h later at regular intervals, 2 days after each restimulation. On the seventh day, after the three rounds of restimulation, cells are harvested and tested the activity of CTL. The stimulated CD8+ cultured cells (CTL) are co-cultured with T2 cells (a human TAP-deficient cell line) pulsed with 2 µg/ml Her-2, gp100, AIM-2, MAGE-1, or IL13 receptor α2 peptides. After 24 hours incubation, IFN-γ in the medium is measured by ELISA assay.

Vaccination (e.g., DC vaccination) can be evaluated in animal models. Suitable models for cancers include injection models, in which cells of a tumor cell line are injected into the animal, and genetic models, in which tumors arise during development.

To evaluate dendritic cell vaccination in an animal model, functional dendritic cells are isolated from bone marrow derived cells of the animal and differentiated in vitro in the presence of cytokines, as detailed above. Mature dendritic cells are pulsed with tumor antigens (e.g., tumor antigens derived from the tumor cell line that will be implanted into the animal or synthetic peptides corresponding to epitopes of those antigens). Animals are implanted with cells of the tumor cell line. After implantation, animals are vaccinated with antigen-pulsed dendritic cells one or more times. Survival and immune responsiveness is measured.

Kits

The present invention is also directed to kits to treat cancers. The kits are useful for practicing the inventive method of treating cancer with a vaccine comprising an antigen or APCs loaded with an antigen as described herein. The kit is an assemblage of materials or components, including at least one of the inventive compositions. Thus, in some embodiments, the kit includes a set of peptides for use in vaccination or preparing cells for vaccination. The kit can also include agents for preparing cells (e.g., cytokines for inducing differentiation of DC in vitro). The invention also provides kits containing a composition including a vaccine comprising dendritic cells (e.g., cryopreserved dendritic cells) loaded with the antigens as described herein.

The exact nature of the components configured in the inventive kit depends on its intended purpose. For example, some embodiments are configured for the purpose of treating brain cancer, colon cancer, hepatocellular carcinoma, prostate cancer, multiple myeloma, and melanoma. In one embodiment the brain cancer is a glioma. In another embodiment, the brain cancer is glioblastoma multiforme (GBM). In another embodiment, the brain cancer is an astrocytoma. In one embodiment, the kit is configured particularly for the purpose of treating mammalian subjects. In another embodiment, the kit is configured particularly for the purpose of treating human subjects. In further embodiments, the kit is configured for veterinary applications, treating subjects such as, but not limited to, farm animals, domestic animals, and laboratory animals.

Instructions for use can be included in the kit. "Instructions for use" typically include a tangible expression describing the technique to be employed in using the components of the kit to effect a desired outcome, such as to treat cancer. For example, the instructions can include instructions to administer a vaccine (e.g., comprising dendritic cells loaded with the antigens described herein) to the patient. Instructions for use can also include instructions for repeated administrations of the vaccine; for example, administering the three doses of the vaccine in two week intervals.

Optionally, the kit also contains other useful components, such as, diluents, buffers, pharmaceutically acceptable carriers, syringes, catheters, applicators, pipetting or measuring tools, or other useful paraphernalia as will be readily recognized by those of skill in the art.

The materials or components assembled in the kit can be provided to the practitioner stored in any convenient and suitable ways that preserve their operability and utility. For example the components can be in dissolved, dehydrated, or lyophilized form; they can be provided at room, refrigerated or frozen temperatures. The components are typically contained in suitable packaging material(s). As employed herein, the phrase "packaging material" refers to one or more physical structures used to house the contents of the kit, such as inventive compositions and the like. The packaging material is constructed by well known methods, preferably to provide a sterile, contaminant-free environment. The packaging materials employed in the kit are those customarily utilized in cancer treatments or in vaccinations. As used herein, the term "package" refers to a suitable solid matrix or material such as glass, plastic, paper, foil, and the like, capable of holding the individual kit components. Thus, for example, a package can be a glass vial used to contain suitable quantities of a composition containing a vaccine, e.g., a vaccine comprising an immunogen or dendritic cells loaded with the antigens as described herein. The packaging material generally has an external label which indicates the contents and/or purpose of the kit and/or its components.

EXAMPLES

The following Examples are illustrative and not limiting.

Example 1

CD133 HLA-A2 Restricted Epitopes

An HLA-A2 epitope of human CD133, ILSAFSVYV (SEQ ID NO:1) was identified. To demonstrate that the peptide binds to HLA-A2 molecules, T2 cells were incubated overnight with 100 µM of each peptide identified in Table 1. The cells were then incubated with Brefeldin A (Sigma, St. Louis, Mo.) at 10 µg/ml for 1 hour, washed, incubated at 37° C. for 0, 3, or 6 hours in the presence of Brefeldin A (0.5 µg/ml), and then stained with BB7.2 mAb. For each time point, peptide-induced HLA-A*0201 expression (MFI) was calculated as: mean fluorescence of peptide preincubated T2 cells—mean fluorescence of T2 cells treated in similar conditions in the absence of peptide. DC50 was defined as the time required for the loss of 50% of the HLA-A*0201/peptide complexes stabilized at t=0. SEQ ID NO:1 bound strongly to the HLA-A2 molecules.

TABLE 1

Binding of Peptides to HLA-A2

| Peptide | Sequence | SEQ ID NO | MFI 0 hour | 3 hour | 6 hour | DC50 |
|---|---|---|---|---|---|---|
| CD133-117 | LLFIILMPLV | 2 | 5.5 | 7.5 | 1.01 | |
| CD133-301 | SLNDPLCLV | 3 | 10.69 | 14.3 | 13.3 | |
| CD133-405 | ILSAFSVYV | 1 | 79.69 | 69.26 | 44.5 | >6 h |
| CD133-708 | GLLERVTRI | 4 | 13.07 | 14.81 | 1.3 | |
| CD133-804 | FLLPALIFAV | 5 | 89 | 67.59 | 34.7 | |
| gp100-209-2M | IMDQVPFSV | 15 | 49.41 | 32.13 | 30.5 | |

To generate peptide-specific CTLs, CD8(+)T cells were isolated from healthy donors, then stimulated by autologous DC pulsed with peptide. Specific T cells were generated after PBMCs were stimulated by autologous DC pulsed with irradiated, apoptotic cancer stem cells (CSCs). Phycoerythrin-conjugated HLA-A*0201/peptide tetramers were synthesized. The cells were stained with tetramers (5 ng/ml) in PBS+0.5% human AB serum for 1 hour at room temperature, washed once in the same buffer, stained with anti-human CD8-FITC (BD Biosciences) mAbs for 30 minutes at 4° C. followed by flow cytometry analysis. It was found that there were 3.72% Tetramer 405 positive cell (SEQ. ID NO:1), which was much higher (FIG. 1) than the other four peptides tested (FIGS. 2, 3, 4, and 5 show the results for the peptides of SEQ ID NOs 2, 3, 4, and 5, respectively).

The binding of the peptide-primed CTLs to HLA-A2 positive human cells was also tested. To generate dendritic cells, the plastic adherent cells from PBMCs were cultured in AIM-V medium supplemented with recombinant human GM-CSF and recombinant human IL-4 at 37° C. in a humidified incubator with 5% $CO_2$. Six days later, the immature dendritic cells were stimulated with recombinant human TNF-alpha for maturation. Mature dendritic cells were then harvested on day 8, resuspended in PBS at $1 \times 10^6$/mL with the indicated peptides (2 μg/mL), and incubated for 2 hours at 37° C. Autologous PBMCs ($2 \times 10^6$ per well) were cocultured with $2 \times 10^5$ per well peptide-pulsed dendritic cells in 2 mL/well of AIM-V medium supplemented with 5% human AB serum and 10 units/mL rhIL-7 (Cell Sciences) in each well of 24-well tissue culture plates.

On the next day and then every 3 days thereafter, 300 IU/ml of IL-2 was added to the medium. On day 7, lymphocytes were restimulated with autologous dendritic cells in AIM-V medium supplemented with 5% human AB serum, rhIL-2, and rhIL-7 (10 units/mL each). To generate peptide-specific CTLs, CD8(+)T cells were isolated from healthy donors, then stimulated by autologous DC pulsed with peptide. After three cycle stimulations, these CTLs could efficiently recognize both HLA-A2 and CD133 positive cancer stem cells, as measured by amount of IFN-γ (pg/ml) in supernatant detected by ELISA (Table 2). However, they could not recognize the CD133 positive normal neural stem cells due to their absence of MHC expression. These findings demonstrated that CD133 derived epitopes could be naturally processed and presented by their autologous MHC on the cell surface.

TABLE 2

Binding of peptide-stimulated CTLs to HLA-A2 and CD133+ CSCs

| Target | IFN-γ (pg/ml) induced by PBMC stimulus for CTL generation | | | | |
|---|---|---|---|---|---|
| | peptide 117 | peptide 301 | peptide 405 | peptide 708 | peptide 804 |
| T2 only | 275 | 179 | 289 | 206 | 211 |
| T2 + 117 | 322 | 174 | 334 | 281 | 275 |
| T2 + 301 | 247 | 165 | 311 | 234 | 148 |
| T2 + 405 | 262 | 185 | 2450 | 326 | 294 |
| T2 + 708 | 192 | 214 | 394 | 286 | 247 |
| T2 + 804 | 336 | 252 | 390 | 258 | 409 |
| CSC4 | 262 | 390 | 2311 | 403 | 450 |

Figure 6:
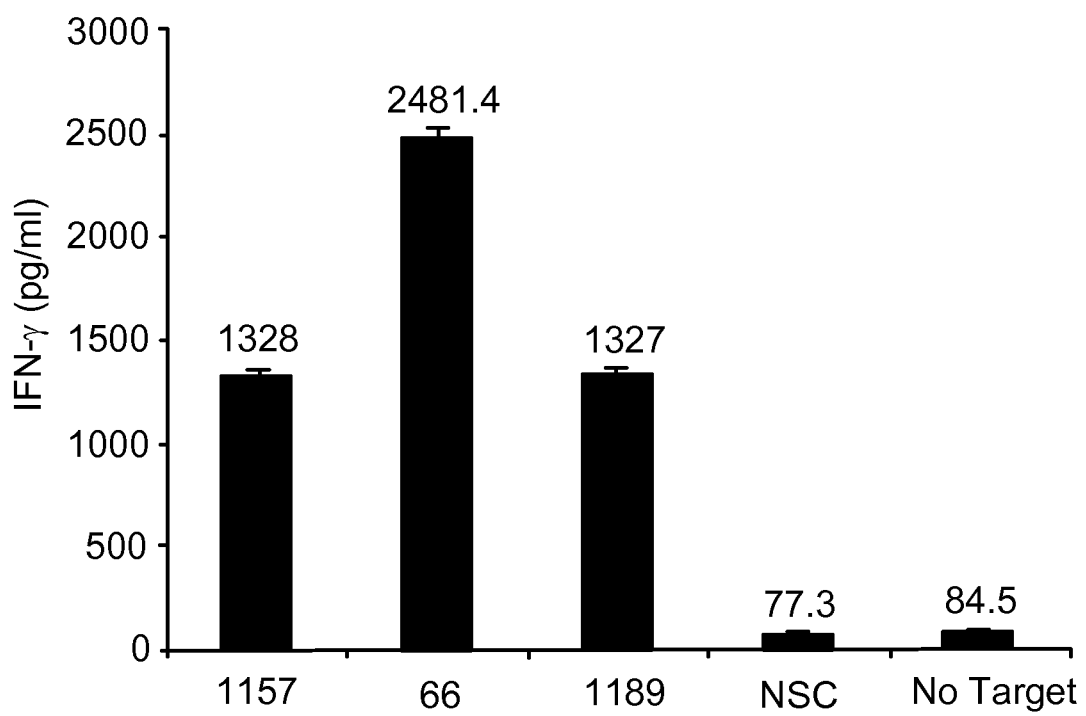
FIG. 6 is a bar graph depicting IFN-γ production by CD8$^+$ T cells challenged with the indicated cells. The CD8$^+$ T cells were previously primed in vitro with dendritic cells that were cultured in the presence of irradiated glioblastoma multiforme (GBM) cancer stem cells (CSCs).

To test whether monocyte-derived dendritic cells (MoDCs) could cross-present peptide 405 through acquisition of apoptotic bodies from GBM CSCs, MoDCs were cultured in the presence of irradiated GBM CSC line 4 and used to prime CSC antigen-specific CD8+ T cells in vitro. As shown in FIG. 6, a significantly high level of IFN-γ (2481±46 pg/ml) was produced when the primed CTL culture was mixed with the GBM CSC line 66 as compared to HLA null normal neural stem cells (77±7 pg/ml) and no target control (85±9 pg/ml).

Figure 7:
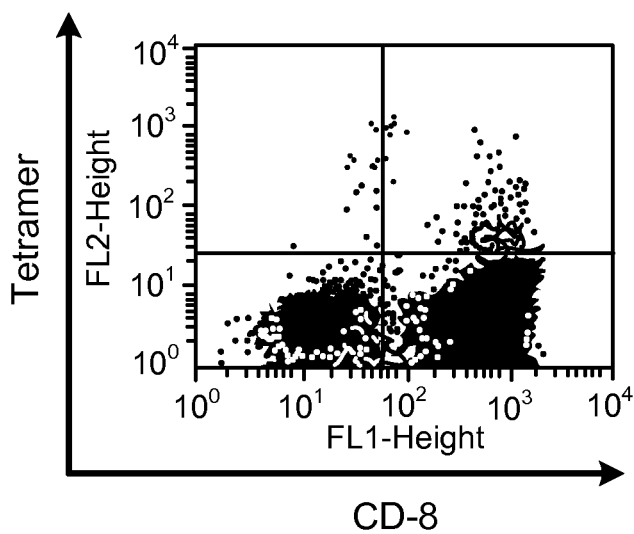
FIG. 7 is a scatter plot of a flow cytometry analysis of GBM CSC induced CTLs stained with phycoerythrin-conjugated HLA-A*0201/peptide 405 tetramers (y-axis) and anti-human CD8-FITC mAbs (x-axis).

The primed CTL culture also was co-cultured with two other CSC lines, lines 1157 and 1189, and again significantly higher levels of IFN-γ (1328±29 and 1327±7 pg/ml respectively) than controls were detected. However, these levels were significantly lower than the level when primary GBM CSC line 4 was used as a target (FIG. 6). Tetramer staining of the CTL priming culture showed the presence of peptide 405-specific CTLs, and the frequency was comparable to that of the CTL priming culture using peptide 405-pulsed MoDCs, possibly contributing a majority of IFN-γ production (FIG. 7).

Overall, these results show that peptide 405 binds relatively strongly to HLA-A*0201 molecule and is highly immunogenic. Peptide 405 most likely represents an immunodominant CD133 epitope restricted by HLA-A*0201 allele and is suitable for immunotherapy.

Example 2

Superagonist CD133 Peptides

Superagonist peptides of the CD133 epitopes described herein are produced by the methods described below. These peptide superagonists exhibit a superior capacity to induce CTL responses.

For this application T cell lines and clones are generated from peripheral blood mononuclear cells (PBMC) derived from glioma patients. Epstein Barr transformed autologous B cells are used as antigen presenting cells through all the T cell functional assays and stimulations. Blood is obtained from glioma patients and carefully layered on top of 50 ml conical tubes (polypropylene, Sarsted) in a ratio of 2 volumes per 1 volume of Histopaque® reagent (Sigma, St Louis, Mo.). Each tube is then placed in a clinical swing out centrifuge (Beckman) and spun down for 30 minutes at 400 g at room temperature. The PBMC are then collected from the interface with a transfer plastic pipette (Samco) and washed 2× with D-PBS at 250 g and 1× with culture medium (IMDM, Biowhittaker, Walkersville, Md.) containing 8% AB human serum (Gemini Bio-products, Woodland, Calif.) at 200 g for 10 minutes each step. The supernatant is aspirated and discarded, and the cells are resuspended in culture medium.

CD8+ and CD4+ T cells are isolated from PBMC by positive selection following manufacturer's instructions (CD8 and CD4 positive selection kits, Dynal Biotech Inc., Lake Success, N.Y.). The isolated cells are used immediately for stimulation protocols.

Transformation of B cells from PBMC by Epstein Barr virus (EBV) is performed immediately after PBMC isolation. Briefly, frozen PBMCs are thawed, washed, and resuspended in CRPMI 10% FBS. 5 to 10 million PBMCs are resuspended in 2.5 ml of CRPMI 10% FBS. Then, 2.5 ml of thawed supernatant from B95.8 Marmoset cells (containing the EBV) are added to each conical tube containing the cells. The cells are incubated for 2 hours in a water bath at 37° C. CRPMI 10% FBS containing 1 μg/ml of Cyclosporin A is then added to each tube. 10 ml suspensions are transferred to T-25 flasks and incubated for 3 weeks. At this point, the cells form clumps visible to the naked eye. By microscopic examination, the cells appear large, clear and possibly hairy. These are indicators of B cell immortalization by EBV. Cells are mixed in their flasks and the 10 ml culture is split into 2 new T-25 flasks (5 ml each). 5 ml of fresh CRPMI-10 media containing 1 μg/ml cyclosporin A is added to each flask and the cultures are incubated for 1 week at 37° C. At this time point, an aliquot of each donor's cells is stained for CD19 expression (Pharmingen anti-CD19-APC stain) and analyzed by flow cytometry. The cell lines are then expanded and frozen down at 5×10⁶/vial. Immortalized B cells are expanded in culture by splitting 1:3 in CRPMI-10 media (without cyclosporin A) in T-25 flasks once a week and incubating at 37° C., 5% $CO_2$. These lymphoblastoid B cell lines (EBV-LCL) are used as antigen presenting cells in the following T cell functional assays.

PBMC are stimulated with the reported CD133 antigens and with cancer stem cell lines in the presence of autologous dendritic cells. Briefly, T cells derived from either single well or multiple wells (bulk cultures) are used after 6-7 days of stimulation. T cell limiting dilutions are done at a concentration of 0.3, 1, 3 and 10 cells/well in 96-well round bottom plates (Corning). 1×10⁵ irradiated autologous dendritic cells per well are added together with IL-2 and IL-7 (20 U/ml and 10 ng/ml, respectively). About five to ten times the original number of the plated cells is obtained. Wells that demonstrate growth are expanded by restimulation with a larger number of irradiated allogeneic feeders, PHA, and IL-2 until sufficient numbers are obtained for specificity tests. At this point, some cells are frozen while others are tested for antigen reactivity by using different readouts of T cell activation, namely cytokine production, cell killing and proliferation. Multiplex cytokine assay (Millipore, Billerica, Mass.) is performed according to the manufacturer's instructions to quantify, in an unbiased manner, a large cytokine spectrum to determine the best cytokine(s) for the evaluation of antigen specificity.

TCR profiles of the generated T cell clones are obtained to demonstrate and monitor clonality. The Vβ repertoire is determined using flow cytometry (as described above) with specific mAbs (available through Immunotech, Miami, Fla.) for cells that expand to large numbers (>10 million). At this point, clones generated against cancer stem cells are tested with a panel of known tumor antigens to make sure that these cells are of "unknown peptide" specificity before stepping to the screening of combinatorial libraries.

Immortalization of the antigen-responsive human T cells from PBMCs provides an advantage for the study of their fine specificity with the combinatorial libraries, because a high number of T cells are needed for the screening of these libraries. Indeed, in order to obtain adequate data from combinatorial libraries, cells should be grown to a minimal of 30 to 100 million cells. For this reason, the defined T cell lines and clones are immortalized. Briefly, transduction is obtained by magnetofection in dividing T cells (recently stimulated), which are washed, counted, and plated with 100 U/ml of IL-2 in complete medium in 96 well plates (flat bottom). A mixture of the retroviral vector with Viromag R/L (OZ Biosciences) is incubated for 20 minutes before being layered onto the T cells, and the plate is then carefully set on the top of magnetic plate and incubated overnight. The next day the cells are resuspended in fresh complete medium with IL-2 and transferred to a larger well. After 48 hours the transfection efficiency is assessed by flow cytometry by staining with phycoerythrin (PE)-conjugated anti-nerve growth factor receptor antibody. Magnetic bead enrichment of transduced cells is performed according to Miltenyi protocols using anti-PE beads (Miltenyi).

CD133-specific T cell lines and clones are obtained within 2-4 months from the primary stimulation.

Combinatorial peptide libraries for screening for superagonist peptides are prepared as described previously in Pinilla et al., 1994, Biochem. J., 301:847-853.

T cell functional assays are performed in 96-well plates (Corning Inc., Corning, N.Y.). Each plate can accommodate 80 samples in columns 3-12, with the first 2 columns reserved for negative and positive control wells. The dispensing of samples and common reagents is accomplished using a Precision™ automated liquid handling instrument (Biotek, Winooski, Vt.). All samples, both libraries and individual compounds, are stored in 96-tube racks that are compatible with both the 96-well plates and the liquid handler instrumentation. Thirty plates per week are tested with the T cell functional assays. For assays that are run in duplicate, this generates approximately 1,000 data points per week. Data are acquired in the instruments specified for each type of assay and transferred to specifically designed Excel™ workbooks for rapid and accurate analysis.

Library mixtures are tested at a final concentration of 100 or 200 µg/ml using the general plate layout described above. Briefly, 25,000 T cells are cultured in the presence of 50,000 irradiated autologous lymphoblastoid cell lines (LCLs) and 25 µl of each mixture library at 2 mg/ml in complete RPMI. Each mixture is tested in duplicate. Control wells include T cells and LCLs without mixtures and with or without phytohemagglutinin (at a final concentration of 5 µg/ml). As mentioned before for antigen specificity, different readouts of T cell activation are tested to confirm the assay readout that provides the best signal for the screening with the libraries. After the screening with the library, the results are used to design individual peptides by combining the selection of the defined amino acids of the most active mixtures at each defined position. This approach provides optimized agonists and superagonist peptides of the CD133 epitopes described herein. The most active peptides are selected to determine their in vitro immunogenicity and cross reactivity with the native antigen.

Individual agonist and superagonist peptides are synthesized by the simultaneous multiple peptide synthesis method (Houghten, 1985, Proc. Natl. Acad. Sci. USA, 82:5131-35). The purity and identity of each peptide are characterized using an electrospray mass spectrometer interfaced with a liquid chromatography system.

To test the stimulatory capacity of the peptides, 25,000 T cells are cultured in the presence of 50,000 irradiated autologous LCLs and each of the individual peptides at a final concentration of 10 and 1 µg/ml. The stimulatory activity of the positive peptides is determined with dose-titration experiments to determine the concentration that yields 50% stimulatory activity (EC-50).

These studies identify superagonist peptides derived from the CD133 described herein. Strong agonist peptides recognized with EC-50 values in the nanomolar range are identified.

Example 3

Immunization with CD133 Peptides

Vaccination with CD133 A2 epitope peptides and superagonists is tested for killing of tumors in humanized HLA A2 transgenic mice. The efficacy of vaccination with CD133 epitope and its superagonists with regard to peripheral cytotoxicity, intracranial tumor infiltration, and survival is tested.

Briefly, HHD mice are immunized with CD133-405 or each of the peptide superagonists described herein emulsified in Incomplete Freund's adjuvant and helper antigen. Bulk populations of splenocytes are tested for specific cytotoxicity against the EL4-HHD cells pulsed with CD133405, control unpulsed EL4-HHD, or EL4-HHD-CD133405 cells. Measurement of the peptide/HLA-A2 complex binding and stability is performed. Survival of animals vaccinated with CD133 epitope superagonists is compared with that of mock immunized mice.

CD133 peptides and superagonists are synthesized by N-(9-fluorenyl) methoxycarbonyl chemistry at >95% purity as indicated by analytic high-performance liquid chromatography and mass spectrometric analysis. Peptides are dissolved in PBS/10% DMSO at a concentration of 2 mg/ml and stored at −20° C. until use.

The peptides are tested in HHD mice, which are humanized with regard to HLA-A2 expression (Pascolo et al., 1997, J. Exp. Med., 185:2043-51). The HHD mice used are Dbcβ2 microglobulin null and transgenic for modified HLA-A*0201-β2 microglobulin single chain (HHD) (Eguchi et al., 2006, Cancer Res., 66:5883-91; Gross et al., 2004, J. Clin. Invest., 113:425-433).

An HHD-syngeneic tumor cell line that expresses CD133 is created. The full-length human CD133 cDNA fragment is generated by reverse transcription-PCR using forward (AGTATGGCTTTCGTTTGCTTGGC; SEQ ID NO:16) and reverse (TACCGAGCTCGGATCCACTAGT; SEQ ID NO:17) primers and CSC1 glioblastoma multiforme cancer stem cell-derived total RNA. The CD133 cDNA is then cloned into the expression plasmid pEF6/V5-His-TOPO vector (Invitrogen) to generate pEF6/V5-CD133. EL4-HHD cells are then transfected with the pEF6/V5-CD133 using Cell Line Nucleofector kit T (Amaxa, Gaithersburg, Md.), and a blasticidine-resistant clone that stably expresses the highest level of CD133 based on flow-cytometry using CD133 mAb (Tessa) is selected (EL4-HHD-CD133) for further use.

Cells are stained with phycoerythrin-conjugated HLA-A*0201/SEQ ID NO:1 tetramers (10 µg/mL) in PBS containing 1% bovine serum albumin for 15 minutes at room temperature, washed once, and stained with FITC-conjugated anti-human CD8 or anti-mouse CD8 (BD Biosciences, San Diego, Calif.). Flow cytometric analyses are performed using Coulter EPICS cytometer (Beckman Coulter, Fullerton, Calif.).

To measure the peptide/HLA-A2 complex binding and stability, T2 cells ($1 \times 10^6$ cells/mL) are incubated with various concentrations (0.1-100 nmol/L) of peptides in serum-free RPMI 1640 at 37° C. overnight in an atmosphere containing 5% $CO_2$. The cells are then washed twice with PBS and stained with the BB7.2 mAb for 30 minutes at 4° C. After washing, FITC-conjugated goat anti-mouse IgG (Caltag, Burlingame, Calif.) is used as the secondary antibody. Surface expression levels of HLA-A2 are examined by flow cytometry. Peptide binding is evaluated by determining mean fluorescence intensity (MFI).

HHD mice are vaccinated (on days 0 and 7) with s.c. injections of 100 µg of CD133-405 or each of the peptide superagonists emulsified in Incomplete Freund's adjuvant (IFA; Difco, Detroit, Mich.) in the presence of 140 µg of the I-Ab-restricted HBVcore128 T-helper epitope, which stimulates a CD4+ helper T-cell response. Control animals receive IFA containing HBV helper-peptide only. On day 11 after the second immunization, the animals are sacrificed, and $5 \times 10^7$ splenocytes are stimulated in vitro with the same peptide that is used for in vivo stimulation (10 µmol/L). On day 6 of culture, the bulk populations are tested for specific cytotoxicity against EL4-HHD or EL4-HHD-CD133-405 cells.

To assess systemic protective immunity against i.c. tumor challenge, on day 7 after the second immunization, HHD mice receive an i.c. inoculation of EL4-HHD-CD133-405 cells. Briefly, $5 \times 10^4$ EL4-HHD-CD133-405 cells are stereotactically injected through an entry site at the bregma 2 mm to the right of the sagittal suture and 3 mm below the surface of the skull of anesthetized mice using a stereotactic frame. The animals are monitored daily after treatment for the manifestation of any pathologic signs.

Mice bearing i.c. EL4-HHD-CD133-405 tumors receive immunizations on days 14 and 21 after the tumor inoculation, sacrificed by $CO_2$ asphyxiation on day 28, and perfused through the left cardiac ventricle with PBS. Brains are enzymatically digested (Walker et al., 2000, J. Immunol., 165 3128-35; Calzascia et al., 2005, Immunity, 22:175-184), and cells from each brain are resuspended in 70% Percoll (Sigma, Saint Louis, Mo.), overlaid with 37% and 30% Percoll and centrifuged for 20 minutes at 500×g. Enriched brain-infiltrating lymphocyte (BIL) populations are recovered at the 70% to 37% Percoll interface.

Survival data are compared using a log-rank test. Comparative numbers of T-cell responses are analyzed by Student's t test for two samples with unequal variances. Statistical significance is determined at the <0.05 level. Positive response is also defined as follows: the specific lysis by the responder cells against antigen-positive target cells is at least 15% and 2-fold higher than lytic levels by corresponding control conditions in at least two effector/target (E/T) ratios. Post-hoc contrasts (e.g., Students' 't' test) are performed to determine significant differences, i.e., p<0.05 between the 3 groups of animals receiving epitope vaccination, control vaccinations, and PBS vehicle control. Ten animals/group are used, sufficient to detect a 1.2 SD difference between groups at a power of 0.8 and a p=0.05.

Brain inflammation in response to vaccination is measured by performing a quantitative stereological analysis of the infiltration of T, B, and NK lymphocytes and macrophages. An immune cellular infiltrate is detected only in the intracranial tumor. Influx of CD4+, CD8+, and NK cells is observed within the tumor and peritumoral area. Increased activation of astrocytes is also observed, as evidenced by up-regulation of GFAP immunoreactivity in astrocytes.

Example 4

Activity of CD133 Superagonist Peptides

The capacity of CD133 superagonist peptides to induce CTLs capable of cross-reacting against the wild-type epitope is determined. HLA-A2-binding and stability assays are performed to determine whether the improved immunogenicity of the analog peptides is at least partially attributable to higher binding/stability of these superagonist peptides in HLA-A2 complexes that are required for specific CTL recognition. CTL assays analyzing reactivity versus peptide dose titration on T2 target cells are performed to detect whether the CTLs developed using the superagonist peptides possesses a higher functional avidity than those primed with wild-type peptide. CTL clones raised against the agonistic peptide-epitope have a more restricted T cell receptor (TCR) usage and higher TCR functional avidity than the CTL clones raised against the natural peptide-epitope.

PBMCs are obtained from glioma patients and healthy donors under an Institutional Review Board—approved protocol. HLA-A2 expression on the PBMC is validated using the monoclonal antibodies (mAb) MA2.1 (against HLA A2, B17) and BB7.2 (against HLA A2, Aw69: both from the American Type Culture Collection, Manassas, Va.) in indirect immunofluorescence assays monitored by flow cytometry.

HLA-A*0201 restricted CTL clones specific for CD133 natural and superagonist peptide-epitopes are generated in vitro. Harvested mature monocyte derived dendritic cells (mMoDC) are pulsed with natural and superagonist peptides (20 µM) and, after washing, are mixed with magnetically enriched CD8+ T cells from either thawed cryopreserved CD14 negative PBMCs or fresh PBMCs. Peptide pulsed mMoDC and enriched CD8+ T cells are mixed at a ratio of 1:20 in the presence of sCD40L (2 µg/ml) to initiate Th1-polarization of mMoDC, which boosts IL-12 production (Mailliard et al., 2002, J. Exp. Med., 195:473-483; Mailliard et al., 2004, Cancer Res., 64: 5934-37). On day three, the priming culture is supplemented with IL-2 (50 U/ml) and IL-7 (10 U/ml), and on day 12 the culture is restimulated with peptide pulsed autologous PBMC. At day 24-28, the priming culture is tested by tetramer staining for the presence of expanded primed CTL specific for the peptide used. As a positive control, priming with HLA-A*0201 restricted p24HIV-1 (SLYNVATL; SEQ ID NO:18) is run concurrently (Kan-Mitchell et al., 2006, J. Immunol., 176:6690-6701; Mitchell et al., 2007, Cancer Immunol. Immunother., 56:287-301).

For assessment of stability, patient-derived T2 cells ($1\times10^6$ per mL) are incubated overnight with 100 µmol/L of each peptide in serum-free RPMI 1640 at 37° C. Thereafter, the cells are washed four times to remove free peptides and incubated at 37° C. for 0, 3, or 6 hours. The cells are stained with the BB7.2 mAb to evaluate the HLA-A2 molecule expression at each time point. Peptide-induced HLA-A2 expression is evaluated by calculating the mean fluorescence of peptide-incubated T2 cells minus the mean fluorescence of T2 cells in the absence of peptide. DC50 is measured as the time required for the loss of 50% of the HLA-A2/peptide complexes stabilized at t=0.

TCR usage of CTL clones is determined by expression of variable region of β chain (V-β) of TCR. Expression of TCR-V-β and V-α among clonally expanded CD8 T cells is assessed by a real-time PCR using a fluorogenic probe (Lang et al., 1997, J. Immunol. Methods, 203:181-192). This method offers a similar degree of sensitivity to the conventional detection of TCR-V-β expression with reduced processing time. Briefly, total RNA extraction and reverse transcription are performed. In the PCR step, a V-β-specific 5' probe, common CB 3' primers, and an internal fluorogenic probe are used to amplify 26 possible V-β genes. The detection and quantitation of PCR products are done by using a 7900HT Fast Real-Time PCR System (Applied Biosystems), with which it is possible to calculate the semi-quantitative ratio of TCR V-β expression among clonally expanded CD8 T cells. Once the expression of a particular TCR V-β is determined, using the same V-β specific primer the sequence corresponding to CDR 3 is determined. This allows for delineation of the clonality of CTLs.

Tetramer decay analysis is performed to determine TCR avidity of the CTL clones (Savage et al., 1999, Immunity, 10:485-492). CTL clones are stained with tetramer (1-25 nM), as in the equilibrium binding experiments above. Cells are washed twice with FACS buffer (4% FCS and 0.1% sodium azide in PBS) and kept on ice until they are mixed with excess anti-HLA-A02 mAb (BB7.2, BD Biosciences) and then incubated at room temperature to allow for tetramer dissociation. The anti-HLA-A02 mAb is used to block rebinding of tetramer to the TCR. Dissociation is followed for 0-180 minutes, after which cells are washed quickly with ice-cold buffer to remove all unbound tetramer and blocking mAb. The cells are then fixed for flow cytometry analysis (CyanADP, Beckman-Coulter). The natural logarithm of percentage of Geometric Mean Fluorescence (GMF) at each time point (compared with 0 minutes) is plotted against time. The half-life of each pMHC multimer is derived from the slope by the equation $t_{1/2}=\ln_2/\text{slope}$.

CTL activity of the in vitro primed CTL clones is measured by flow cytometric assay (Betts et al., 2003, J. Immunol. Methods, 281:65-78; Betts et al., 2004, Methods Cell Biol., 75:497-512). Briefly, the priming culture containing the CTL clone is mixed 1:1 with peptide pulsed T2 cells for 6 hours in the presence of CD107a, Monensin, and Brefeldin A. After the 6 hour incubation, cells are stained with corresponding tetramers and anti-CD8 mAb, followed by intracellular IFN-γ and TNFα staining Stained cells are run on Beckman-Coulter CyAn™ ADP analyzer (9 color, 11 parameters) for flow cytometric analysis. All the assays are run in triplicate.

To measure cytotoxicity, targets are labeled with 100 µCi of $^{51}$Cr for 60 minutes, plated in 96-well V-bottomed plates ($3\times10^3$ cell/well), and pulsed with peptides (1 µM) at 37° C. for 2 hours. Effectors are added and incubated at 37° C. for an additional 4 hours. One hundred microliters of supernatant are collected, and the radioactivity is measured in a gamma counter. The percentage of specific lysis is determined as:

(experimental release−spontaneous release)/(maximal release=Spontaneous Release)×100.

As a surrogate marker for CTL responses, cytokine responses, such as IFN-γ (Mailliard et al., 2004, Cancer Res., 64:5934-37; Herr et al., 2000, Blood, 96:1857-64) and IL-2 (Carrabba et al., 2003, Cancer Res., 63: 1560-67) can be monitored. IFN-γ and IL-2 secretion levels from CTL cultures stimulated with native or superagonist peptides are measured using cytokine-specific ELISA and IFN-γ enzyme-linked immunospot assays.

The relative affinity (RA) of CD133 superagonist peptides for HLA-A*0201 are measured. Briefly, T2 cells are incubated with various concentrations of peptides ranging from 100 to 0.1 µM overnight and then stained with BB7.2 mAb to quantify the surface expression of HLA-A*0201 allele. For each peptide concentration, the HLA-A*0201-specific staining is calculated as the percentage of staining obtained with 100 µM of the reference peptide HIVpol589 (IVGAETFYV; SEQ ID NO:19). The RA is determined as: RA=(concentration of each peptide that induces 20% of HLA-A*0201 expression/concentration of the reference peptide that induces 20% of HLA-A*0201 expression).

The stability of superagonist peptide/HLA-A*0201 complexes is assessed. Briefly, T2 cells are incubated overnight with 100 µM of each peptide. Cells are then incubated with Brefeldin A (Sigma, St. Louis, Mo.) at 10 µg/ml for 1 hour, washed, incubated at 37° C. for 0, 2, 4, or 6 hours in the presence of Brefeldin A (0.5 µg/ml), and then stained with BB7.2 mAb. For each time point, peptide induced HLA-A*0201 expression is calculated as: mean fluorescence of peptide preincubated T2 cells—mean fluorescence of T2 cells treated in similar conditions in the absence of peptide. DC50 is defined as the time required for the loss of 50% of the HLA-A*0201/peptide complexes stabilized at t=0.

CTL are generated from human PBMCs. PBMCs are collected by leukapheresis from healthy HLA-A*0201 volunteers. Dendritic cells are produced from adherent cells ($2\times10^6$ cells/ml) cultured for 7 days in the presence of 500 IU/ml granulocyte macrophage colony-stimulating factor (Leucomax; Schering-Plough, Kenilworth, N.J.) and 500 IU/ml IL-4 (R&D Systems, Minneapolis, Mo.) in complete medium [RPMI 1640 supplemented with 10% heat-inactivated human AB serum, 2 µM L-glutamine (Invitrogen) and antibiotics]. On day 7, dendritic cells are collected and pulsed with 40 µg/ml peptide in the presence of 3 µg/ml β2m (Sigma) for 4 hours at 20° C. and then irradiated (4200 rad). CD8+ T cells are isolated by positive selection with immunomagnetic beads (Miltenyi Biotec, Bergisch Gladbach, Germany)

according to the manufacturer's instructions. A total of 0.5× 10⁶ CD8+ T cells are cocultured with 0.25×10⁵ dendritic cells in a final volume of 0.5 ml/well in a 48-well plate in the presence of 10 ng/ml IL-7 (R&D Systems). Human IL-10 (R&D Systems) at 10 ng/ml is added the next day, and 30 IU/ml human IL-2 (Proleukin; Chiron Corp.) is added on day two. Seven and 14 days after the primary stimulation, CD8+ T cells are restimulated with irradiated adherent cells pulsed with 10 µg/ml peptide in the presence of 3 µg/ml β2m. Human IL-10 (10 ng/ml) and IL-2 (50 IU/ml) are added 24 and 48 hours later, respectively. Seven days after the second restimulation, individual wells from the cultures are tested for peptide specific cytotoxicity on peptide loaded T2 cells in the presence of cold K562 cells (hot/cold target ratio 1:33 ratio).

CTL are also generated from glioblastoma patients. PBMCs from a total of 30 HLA-A2+ glioma patients are evaluated for their in vitro responsiveness against wild-type and superagonist peptides. The proportion of human patients that will develop specific CTLs capable of recognizing the wild-type CD133 peptide after stimulation with the superagonist peptide is determined. It is also determined whether these CTL recognize peptide-pulsed T2 cells or HLA-A2+ cancer stem cell lines that express CD133.

Intracellular production of IFN-γ is detected. A total of 5×10⁴ T cells are incubated with 10⁵ peptide-loaded T2 cells or with 10⁵ tumor cells in the presence of 20 µg/ml Brefeldin A at 37° C. Six hours later, the cells are stained with phycoerythrin-conjugated anti-CD8 mAb (Caltag Laboratories, Burlingame, Calif.) in PBS for 25 minutes at 4° C. and fixed with PBS 4% Paraformaldehyde (Sigma). The cells are then permeabilized with PBS+0.5% BSA+0.2% saponin (Sigma) and stained with adenomatous polyposis coli-conjugated anti-IFN-γ mAb (PharMingen, Mississauga, Ontario, Canada) for 25 minutes at 4° C. Cells are analyzed on a BD FACSCalibur™ flow cytometer (Becton Dickinson, Mountain View, Calif.).

Enzyme-linked immunosorbent spot (ELISPOT) assay kits (R & D Systems, Minneapolis, Mo.) are used to detect immune responses. Responder (R) 1×10⁵ patients' PBMC cells from before and after vaccination are plated in 96-well plates with nitrocellulose membrane inserts coated with capture Ab. Stimulator (S) cells (T2 pulsed potential peptide) are added at the R:S ratio of 1:1. After a 24-hour incubation, cells are removed by washing the plates 4 times. The detection Ab is added to each well. The plates will be incubated at 4° C. overnight, and the washing steps are repeated. After a 2-hout incubation with streptavidin-alkaline phosphatase, the plates are washed. Aliquots (100 µl) of BCIP/NBT alkaline phosphatase substrate solution are added to each well to develop the spots. The reaction is stopped after 60 minutes by washing with water. The spots are scanned and counted with computer-assisted image analysis (Cellular Technology Ltd, Cleveland, Ohio). When experimental values are significantly different from the mean number of spots against non-pulsed T2 cells (background values), as determined by a two-tailed Wilcoxon rank sum test, the background values are subtracted from the experimental values. This assay provides a coefficient of variation of intra-assay for ELISPOT of less than 10%.

The superagonist-induced CTLs possess higher avidity, due to either higher affinity or stability between TCRs and peptide-MHC complexes. The higher avidity correlates with the avidity of T cell-target interactions and the antitumor responsiveness of T cells. The intensity (Yee et al., 1999, J. Immunol., 162:2227-34), or stability (Dutoit et al., 2002, J. Immunol., 168:1167-71) of specific T-cell staining with HLA tetramers, and threshold of positive staining using titrating doses of tetramers (Ercolini et al., 2005, J. Exp. Med., 201: 1591-1602) are indicative of the relative avidity of specific T cells.

Example 5

HLA-A2 Restricted Epitope from Mouse CD133

Figure 8:
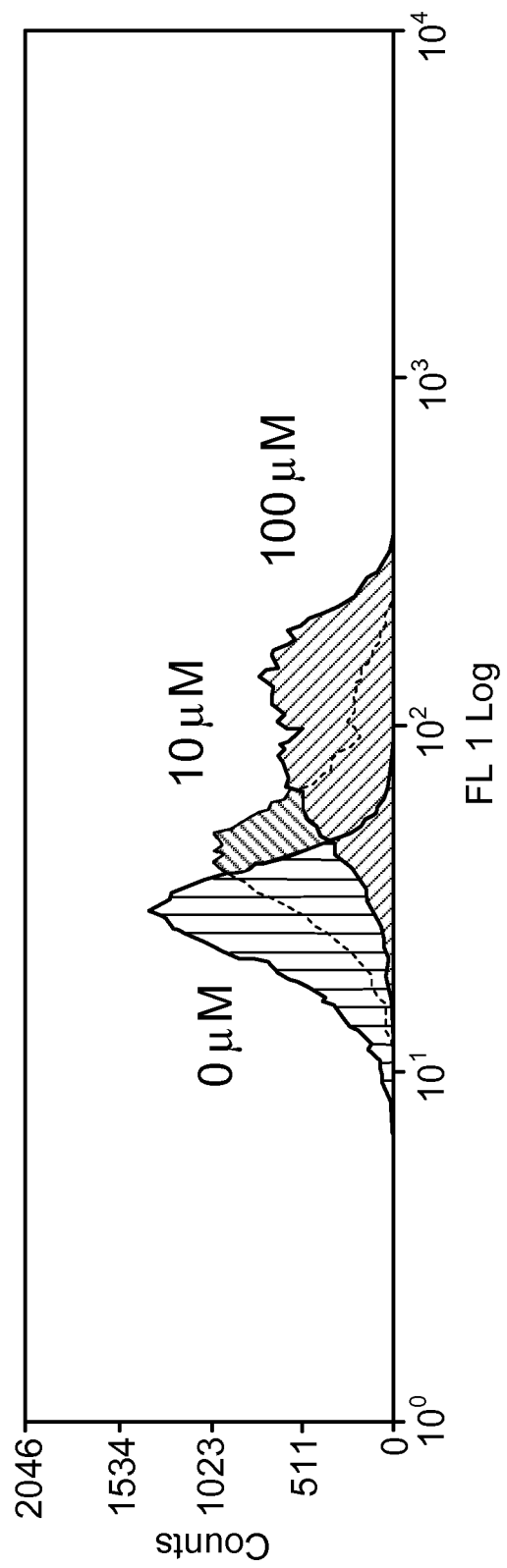
FIG. 8 is a histogram of the number of T2 cells (y-axis) having the indicated fluorescence intensity (x-axis). Fluorescence above the control (0 μM) indicates binding of the mouse peptide (10 μM or 100 μM) to the cells.

The mouse counterpart of SEQ ID NO:1, MLLQVSHYL (SEQ ID NO:11) also bound to HLA-A2, despite having only two amino acid residues in common. T2 cells were incubated overnight with 0 µM, 10 µM, or 100 µM of SEQ ID NO:11. The cells were then incubated with Brefeldin A (Sigma, St. Louis, Mo.) at 10 µg/ml for 1 hour, washed, incubated at 37° C. in the presence of Brefeldin A (0.5 µg/ml), and then stained with BB7.2 mAb. Fluorescence intensity was measured by flow cytometry. Cell fluorescence increased in a dose-dependent manner (FIG. 8), indicating that SEQ ID NO:11 bound to the HLA-A2 molecules. This example indicates that counterparts of SEQ ID NO:1 from other species are also HLA-A2 epitopes.

Other Embodiments

A number of embodiments of the invention have been described. Nevertheless, it will be understood that various modifications may be made without departing from the spirit and scope of the invention. Accordingly, other embodiments are within the scope of the following claims.

What is claimed is:

1. A method of inducing a cytotoxic T lymphocyte (CTL) response in a human subject, the method comprising administering to the subject an effective amount of a composition comprising an isolated immunogen of 9 to 50 amino acid residues comprising a peptide consisting of the amino sequence set forth in SEQ ID NO:1 with four or fewer amino acid substitutions within SEQ ID NO:1, wherein the four or fewer amino acid substitutions do not occur at position 2 or position 8 of SEQ ID NO:1, wherein the peptide is a CD133 HLA-A2 restricted epitope, and wherein the administration of the composition comprising the isolated immunogen elicits a peptide-specific CTL response to cells expressing HLA-A2 and presenting the peptide.

2. The method of claim 1, wherein the composition further comprises an adjuvant, cytokine, or vehicle.

3. A method of inducing a therapeutic cytotoxic T lymphocyte (CTL) response in a mammalian subject, the method comprising administering to the subject an effective amount of a composition comprising an isolated peptide having the amino acid sequence selected from the group consisting of SEQ ID NO:1, SEQ ID NO:6, SEQ ID NO:7, SEQ ID NO:8, SEQ ID NO:9, SEQ ID NO:10, and SEQ ID NO:11, with four or fewer amino acid substitutions within said amino acid sequence, wherein the four or fewer amino acid substitutions do not occur at position 2 or position 8 of said amino acid sequence, wherein the peptide is a CD133 HLA-A2 restricted epitope, and wherein the administration of the composition elicits a peptide-specific CTL response to cancer cells expressing HLA-A2 and presenting the peptide.

4. The method of claim 3, wherein the peptide consists of the sequence set forth in SEQ ID NO:1.

5. The method of claim 3, wherein the peptide consists of the sequence set forth in SEQ ID NO:11.

6. The method of claim 1, wherein the isolated immunogen is 9 to 30 amino acids in length and comprises a peptide consisting of the amino acid sequence set forth in SEQ ID NO:1 with four or fewer amino acid substitutions within SEQ ID NO:1, wherein the four or fewer amino acid substitutions do not occur at position 2 or position 8 of SEQ ID NO:1.

7. The method of claim 1, wherein the isolated immunogen is 9 to 30 amino acids in length and comprises a peptide consisting of the amino acid sequence set forth in SEQ ID NO:1 with two or fewer amino acid substitutions within SEQ ID NO:1, wherein the two or fewer amino acid substitutions do not occur at position 2 or position 8 of SEQ ID NO:1.

8. The method of claim 1, wherein the isolated immunogen is 9 to 30 amino acids in length and comprises a peptide consisting of the amino acid sequence set forth in SEQ ID NO:1.

9. The method of claim 1, wherein the isolated immunogen is 9 to 20 amino acids in length and comprises a peptide consisting of the amino acid sequence set forth in SEQ ID NO:1 with four or fewer amino acid substitutions within SEQ ID NO:1, wherein the four or fewer amino acid substitutions do not occur at position 2 or position 8 of SEQ ID NO:1.

10. The method of claim 1, wherein the isolated immunogen is 9 to 20 amino acids in length and comprises a peptide consisting of the amino acid sequence set forth in SEQ ID NO:1 with two or fewer amino acid substitutions within SEQ ID NO:1, wherein the two or fewer amino acid substitutions do not occur at position 2 or position 8 of SEQ ID NO:1.

11. The method of claim 1, wherein the isolated immunogen is 9 to 20 amino acids in length and comprises a peptide consisting of the amino acid sequence set forth in SEQ ID NO:1.

12. The method of claim 1, wherein the isolated immunogen is 9 to 15 amino acids in length and comprises a peptide consisting of the amino acid sequence set forth in SEQ ID NO:1 with four or fewer amino acid substitutions within SEQ ID NO:1, wherein the four or fewer amino acid substitutions do not occur at position 2 or position 8 of SEQ ID NO:1.

13. The method of claim 1, wherein the isolated immunogen is 9 to 15 amino acids in length and comprises a peptide consisting of the amino acid sequence set forth in SEQ ID NO:1 with two or fewer amino acid substitutions within SEQ ID NO:1, wherein the two or fewer amino acid substitutions do not occur at position 2 or position 8 of SEQ ID NO:1.

14. The method of claim 1, wherein the isolated immunogen is 9 to 15 amino acids in length and comprises a peptide consisting of the amino acid sequence set forth in SEQ ID NO:1.

15. The method of claim 1, wherein the isolated immunogen immunogen is 9 to 12 amino acids length and comprises a peptide consisting of the amino acid sequence set forth in SEQ ID NO:1 with four or fewer amino acid substitutions within SEQ ID NO:1, wherein the four or fewer amino acid substitutions do not occur at position 2 or position 8 of SEQ ID NO:1.

16. The method of claim 1, wherein the isolated immunogen is 9 to 12 amino acids in length and comprises a peptide consisting of the amino acid sequence set forth in SEQ ID NO:1 with two or fewer amino acid substitutions within SEQ ID NO:1, wherein the two or fewer amino acid substitutions do not occur at position 2 or position 8 of SEQ ID NO:1.

17. The method of claim 1, wherein the isolated immunogen is 9 to 12 amino acids in length and comprises a peptide consisting of the amino acid sequence set forth in SEQ ID NO:1.

18. The method of claim 2, wherein the composition comprises an adjuvant.

19. The method of claim 18, wherein the adjuvant is selected from the group consisting of Toll-like receptor agonists, Bacillus Calmette Guerin, complete or incomplete Freund's adjuvant, a cytosine guanine oligodeoxynucleotide, Montanide ISA-51, Activation Gene-3, aluminum phosphate, aluminum hydroxide, alum, and saponin.

20. The method of claim 2, wherein the composition comprises a cytokine.

21. The method of claim 20, wherein the cytokine is selected from the group consisting of Interleukin-1, Interleukin-2, Interleukin-7, Interleukin-12, Interleukin-13, Interleukin-15, tumor necrosis factor, stem cell factor, and granulocyte monocyte colony stimulating factor.

22. The method of claim 3, wherein the composition further comprises an adjuvant, cytokine, or vehicle.

23. The method of claim 1, wherein the four or fewer amino acid substitutions within SEQ ID NO:1 are conservative amino acid substitutions.

24. The method of claim 1, wherein the immunogen comprises a peptide consisting of the amino sequence set forth in SEQ ID NO:1.

25. A method for inducing a cytotoxic T lymphocyte (CTL) dependent immune response in a human subject, the method comprising:

(a) isolating CTLs and autologous dendritic cells (DCs) from the subject;
(b) contacting the CTLs ex vivo with autologous DCs pulsed with a peptide, thereby creating peptide-specific CTLs, wherein the peptide consists of the amino sequence set forth in SEQ ID NO:1 with four or fewer acid substitutions within SEQ ID NO:1;
(c) administering to the subject an effective amount of the peptide-specific CTLs, wherein the peptide-specific CTLs recognize both HLA-A2 and CD133 positive cancer stem cells, thereby eliciting a CD133-specific-CTL response.

26. The method of claim 25, wherein the peptide consists of the sequence set forth in SEQ ID NO:1.

27. The method of claim 25, wherein the subject has cancer.

28. The method of claim 3, wherein the peptide consists of the sequence set forth in SEQ ID NO:6.

29. The method of claim 3, wherein the peptide consists of the sequence set forth in SEQ ID NO:7.

30. The method of claim 3, wherein the peptide consists of the sequence set forth in SEQ ID NO:8.

31. The method of claim 3, wherein the peptide consists of the sequence set forth in SEQ ID NO:9.

32. The method of claim 3, wherein the peptide consists of the sequence set forth in SEQ ID NO:10.

* * * * *

UNITED STATES PATENT AND TRADEMARK OFFICE
CERTIFICATE OF CORRECTION

Page 1 of 1

PATENT NO. : 9,068,020 B2
APPLICATION NO. : 12/552945
DATED : June 30, 2015
INVENTOR(S) : John S. Yu, Keith L. Black and Gentao Liu It is certified that error appears in the above-identified patent and that said Letters Patent is hereby corrected as shown below:

Other Publications

Title page, col. 2 (Other Publications), line 16, delete "Stabilityl" and insert -- Stability -- therefor.

Title page, col. 2 (Other Publications), line 17, delete "Immuno/ogy," and insert -- Immunology, -- therefor.

Claims

Col. 44, lines 51-52, claim 15, delete "immunogen immunogen" and insert -- immunogen -- therefor.

Signed and Sealed this
Eighth Day of December, 2015

Michelle K. Lee
*Director of the United States Patent and Trademark Office*

SEQUENCE LISTING

```
<160> NUMBER OF SEQ ID NOS: 19

<210> SEQ ID NO 1
<211> LENGTH: 9
<212> TYPE: PRT
<213> ORGANISM: Homo sapien

<400> SEQUENCE: 1

Ile Leu Ser Ala Phe Ser Val Tyr Val
1               5

<210> SEQ ID NO 2
<211> LENGTH: 10
<212> TYPE: PRT
<213> ORGANISM: Homo sapien
```

```
<400> SEQUENCE: 2

Leu Leu Phe Ile Ile Leu Met Pro Leu Val
 1               5                  10

<210> SEQ ID NO 3
<211> LENGTH: 9
<212> TYPE: PRT
<213> ORGANISM: Homo sapien

<400> SEQUENCE: 3

Ser Leu Asn Asp Pro Leu Cys Leu Val
 1               5

<210> SEQ ID NO 4
<211> LENGTH: 9
<212> TYPE: PRT
<213> ORGANISM: Homo sapien

<400> SEQUENCE: 4

Gly Leu Leu Glu Arg Val Thr Arg Ile
 1               5

<210> SEQ ID NO 5
<211> LENGTH: 10
<212> TYPE: PRT
<213> ORGANISM: Homo sapien

<400> SEQUENCE: 5

Phe Leu Leu Pro Ala Leu Ile Phe Ala Val
 1               5                  10

<210> SEQ ID NO 6
<211> LENGTH: 9
<212> TYPE: PRT
<213> ORGANISM: Pan Troglodytes

<400> SEQUENCE: 6

Ile Leu Ser Glu Phe Ser Val Tyr Val
 1               5

<210> SEQ ID NO 7
<211> LENGTH: 9
<212> TYPE: PRT
<213> ORGANISM: Canis Lupus Familiaris

<400> SEQUENCE: 7

Lys Leu Ser Asn Phe Met Asp Tyr Ile
 1               5

<210> SEQ ID NO 8
<211> LENGTH: 9
<212> TYPE: PRT
<213> ORGANISM: Equus Caballus

<400> SEQUENCE: 8

Lys Leu Ser Asn Phe Met Asp Tyr Ile
 1               5

<210> SEQ ID NO 9
<211> LENGTH: 9
<212> TYPE: PRT
<213> ORGANISM: Bos Taurus

<400> SEQUENCE: 9
```

```
Thr Leu Ser Asn Phe Val Arg Tyr Ile
 1               5

<210> SEQ ID NO 10
<211> LENGTH: 9
<212> TYPE: PRT
<213> ORGANISM: Rattus Norvegicus

<400> SEQUENCE: 10

Val Leu Leu Gln Phe Ser His Tyr Leu
 1               5

<210> SEQ ID NO 11
<211> LENGTH: 9
<212> TYPE: PRT
<213> ORGANISM: Mus Musculus

<400> SEQUENCE: 11

Met Leu Leu Gln Val Ser His Tyr Leu
 1               5

<210> SEQ ID NO 12
<211> LENGTH: 9
<212> TYPE: PRT
<213> ORGANISM: Artificial Sequence
<220> FEATURE:
<223> OTHER INFORMATION: Synthetic Peptide
<220> FEATURE:
<221> NAME/KEY: VARIANT
<222> LOCATION: 1
<223> OTHER INFORMATION: Xaa = I, K, T, or V
<220> FEATURE:
<221> NAME/KEY: VARIANT
<222> LOCATION: 3
<223> OTHER INFORMATION: Xaa = S or L
<220> FEATURE:
<221> NAME/KEY: VARIANT
<222> LOCATION: 4
<223> OTHER INFORMATION: Xaa = A, E, N, D, or Q
<220> FEATURE:
<221> NAME/KEY: VARIANT
<222> LOCATION: 6
<223> OTHER INFORMATION: Xaa = S, M, V or I
<220> FEATURE:
<221> NAME/KEY: VARIANT
<222> LOCATION: 7
<223> OTHER INFORMATION: Xaa = V, D, R, G or H
<220> FEATURE:
<221> NAME/KEY: VARIANT
<222> LOCATION: (9)...(9)
<223> OTHER INFORMATION: Xaa = V, I or L

<400> SEQUENCE: 12

Xaa Leu Xaa Xaa Phe Xaa Xaa Tyr Xaa
 1               5

<210> SEQ ID NO 13
<211> LENGTH: 9
<212> TYPE: PRT
<213> ORGANISM: Artificial Sequence
<220> FEATURE:
<223> OTHER INFORMATION: Synthetic Peptide
<220> FEATURE:
<221> NAME/KEY: VARIANT
<222> LOCATION: 1
<223> OTHER INFORMATION: Xaa = I, K, T, V or M
<220> FEATURE:
<221> NAME/KEY: VARIANT
<222> LOCATION: 3
<223> OTHER INFORMATION: Xaa = S or L
<220> FEATURE:
```

```
<221> NAME/KEY: VARIANT
<222> LOCATION: 4
<223> OTHER INFORMATION: Xaa = A, E, N, D or Q
<220> FEATURE:
<221> NAME/KEY: VARIANT
<222> LOCATION: 5
<223> OTHER INFORMATION: Xaa = F or V
<220> FEATURE:
<221> NAME/KEY: VARIANT
<222> LOCATION: 6
<223> OTHER INFORMATION: Xaa = S, M, V or I
<220> FEATURE:
<221> NAME/KEY: VARIANT
<222> LOCATION: (7)...(7)
<223> OTHER INFORMATION: Xaa = V, D, R, G or H
<220> FEATURE:
<221> NAME/KEY: VARIANT
<222> LOCATION: (9)...(9)
<223> OTHER INFORMATION: Xaa = V, I or L

<400> SEQUENCE: 13

Xaa Leu Xaa Xaa Xaa Xaa Xaa Tyr Xaa
  1               5

<210> SEQ ID NO 14
<211> LENGTH: 865
<212> TYPE: PRT
<213> ORGANISM: Homo sapien

<400> SEQUENCE: 14

Met Ala Leu Val Leu Gly Ser Leu Leu Leu Gly Leu Cys Gly Asn
  1               5                  10                  15

Ser Phe Ser Gly Gly Gln Pro Ser Ser Thr Asp Ala Pro Lys Ala Trp
                 20                  25                  30

Asn Tyr Glu Leu Pro Ala Thr Asn Tyr Glu Thr Gln Asp Ser His Lys
             35                  40                  45

Ala Gly Pro Ile Gly Ile Leu Phe Glu Leu Val His Ile Phe Leu Tyr
         50                  55                  60

Val Val Gln Pro Arg Asp Phe Pro Glu Asp Thr Leu Arg Lys Phe Leu
 65                  70                  75                  80

Gln Lys Ala Tyr Glu Ser Lys Ile Asp Tyr Asp Lys Pro Glu Thr Val
                 85                  90                  95

Ile Leu Gly Leu Lys Ile Val Tyr Tyr Glu Ala Gly Ile Ile Leu Cys
            100                 105                 110

Cys Val Leu Gly Leu Leu Phe Ile Ile Leu Met Pro Leu Val Gly Tyr
            115                 120                 125

Phe Phe Cys Met Cys Arg Cys Cys Asn Lys Cys Gly Gly Glu Met His
        130                 135                 140

Gln Arg Gln Lys Glu Asn Gly Pro Phe Leu Arg Lys Cys Phe Ala Ile
145                 150                 155                 160

Ser Leu Leu Val Ile Cys Ile Ile Ser Ile Gly Ile Phe Tyr Gly
                165                 170                 175

Phe Val Ala Asn His Gln Val Thr Arg Ile Lys Arg Ser Arg Lys
                180                 185                 190

Leu Ala Asp Ser Asn Phe Lys Asp Leu Arg Thr Leu Leu Asn Glu Thr
                195                 200                 205

Pro Glu Gln Ile Lys Tyr Ile Leu Ala Gln Tyr Asn Thr Thr Lys Asp
            210                 215                 220

Lys Ala Phe Thr Asp Leu Asn Ser Ile Asn Ser Val Leu Gly Gly Gly
225                 230                 235                 240

Ile Leu Asp Arg Leu Arg Pro Asn Ile Ile Pro Val Leu Asp Glu Ile
```

```
                    245                 250                 255
Lys Ser Met Ala Thr Ala Ile Lys Glu Thr Lys Glu Ala Leu Glu Asn
            260                 265                 270

Met Asn Ser Thr Leu Lys Ser Leu His Gln Gln Ser Thr Gln Leu Ser
        275                 280                 285

Ser Ser Leu Thr Ser Val Lys Thr Ser Leu Arg Ser Ser Leu Asn Asp
    290                 295                 300

Pro Leu Cys Leu Val His Pro Ser Ser Glu Thr Cys Asn Ser Ile Arg
305                 310                 315                 320

Leu Ser Leu Ser Gln Leu Asn Ser Asn Pro Glu Leu Arg Gln Leu Pro
                325                 330                 335

Pro Val Asp Ala Glu Leu Asp Asn Val Asn Asn Val Leu Arg Thr Asp
            340                 345                 350

Leu Asp Gly Leu Val Gln Gln Gly Tyr Gln Ser Leu Asn Asp Ile Pro
        355                 360                 365

Asp Arg Val Gln Arg Gln Thr Thr Thr Val Val Ala Gly Ile Lys Arg
    370                 375                 380

Val Leu Asn Ser Ile Gly Ser Asp Ile Asp Asn Val Thr Gln Arg Leu
385                 390                 395                 400

Pro Ile Gln Asp Ile Leu Ser Ala Phe Ser Val Tyr Val Asn Asn Thr
                405                 410                 415

Glu Ser Tyr Ile His Arg Asn Leu Pro Thr Leu Glu Gly Tyr Asp Ser
            420                 425                 430

Tyr Trp Trp Leu Gly Gly Leu Val Ile Cys Ser Leu Leu Thr Leu Ile
        435                 440                 445

Val Ile Phe Tyr Tyr Leu Gly Leu Leu Cys Gly Val Cys Gly Tyr Asp
    450                 455                 460

Arg His Ala Thr Pro Thr Thr Arg Gly Cys Val Ser Asn Thr Gly Gly
465                 470                 475                 480

Val Phe Leu Met Val Gly Val Gly Leu Ser Phe Leu Phe Cys Trp Ile
                485                 490                 495

Leu Met Ile Ile Val Val Leu Thr Phe Val Phe Gly Ala Asn Val Glu
            500                 505                 510

Lys Leu Ile Cys Glu Pro Tyr Thr Ser Lys Glu Leu Phe Arg Val Leu
        515                 520                 525

Asp Thr Pro Tyr Leu Leu Asn Glu Asp Trp Glu Tyr Tyr Leu Ser Gly
    530                 535                 540

Lys Leu Phe Asn Lys Ser Lys Met Lys Leu Thr Phe Glu Gln Val Tyr
545                 550                 555                 560

Ser Asp Cys Lys Lys Asn Arg Gly Thr Tyr Gly Thr Leu His Leu Gln
                565                 570                 575

Asn Ser Phe Asn Ile Ser Glu His Leu Asn Ile Asn Glu His Thr Gly
            580                 585                 590

Ser Ile Ser Ser Glu Leu Glu Ser Leu Lys Val Asn Leu Asn Ile Phe
        595                 600                 605

Leu Leu Gly Ala Ala Gly Arg Lys Asn Leu Gln Asp Phe Ala Ala Cys
    610                 615                 620

Gly Ile Asp Arg Met Asn Tyr Asp Ser Tyr Leu Ala Gln Thr Gly Lys
625                 630                 635                 640

Ser Pro Ala Gly Val Asn Leu Leu Ser Phe Ala Tyr Asp Leu Glu Ala
                645                 650                 655

Lys Ala Asn Ser Leu Pro Pro Gly Asn Leu Arg Asn Ser Leu Lys Arg
            660                 665                 670
```

-continued

```
Asp Ala Gln Thr Ile Lys Thr Ile His Gln Gln Arg Val Leu Pro Ile
            675                 680                 685
Glu Gln Ser Leu Ser Thr Leu Tyr Gln Ser Val Lys Ile Leu Gln Arg
        690                 695                 700
Thr Gly Asn Gly Leu Leu Glu Arg Val Thr Arg Ile Leu Ala Ser Leu
705                 710                 715                 720
Asp Phe Ala Gln Asn Phe Ile Thr Asn Thr Ser Ser Val Ile Ile
                725                 730                 735
Glu Glu Thr Lys Lys Tyr Gly Arg Thr Ile Ile Gly Tyr Phe Glu His
            740                 745                 750
Tyr Leu Gln Trp Ile Glu Phe Ser Ile Ser Glu Lys Val Ala Ser Cys
        755                 760                 765
Lys Pro Val Ala Thr Ala Leu Asp Thr Ala Val Asp Val Phe Leu Cys
    770                 775                 780
Ser Tyr Ile Ile Asp Pro Leu Asn Leu Phe Trp Phe Gly Ile Gly Lys
785                 790                 795                 800
Ala Thr Val Phe Leu Leu Pro Ala Leu Ile Phe Ala Val Lys Leu Ala
                805                 810                 815
Lys Tyr Tyr Arg Arg Met Asp Ser Glu Asp Val Tyr Asp Asp Val Glu
            820                 825                 830
Thr Ile Pro Met Lys Asn Met Glu Asn Gly Asn Asn Gly Tyr His Lys
        835                 840                 845
Asp His Val Tyr Gly Ile His Asn Pro Val Met Thr Ser Pro Ser Gln
    850                 855                 860
His
865

<210> SEQ ID NO 15
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 15

Ile Met Asp Gln Val Pro Phe Ser Val
 1               5

<210> SEQ ID NO 16
<211> LENGTH: 23
<212> TYPE: DNA
<213> ORGANISM: Homo sapien

<400> SEQUENCE: 16
agtatggctt tcgtttgctt ggc                                            23

<210> SEQ ID NO 17
<211> LENGTH: 22
<212> TYPE: DNA
<213> ORGANISM: Homo sapien

<400> SEQUENCE: 17
taccgagctc ggatccacta gt                                             22

<210> SEQ ID NO 18
<211> LENGTH: 8
<212> TYPE: PRT
<213> ORGANISM: Human Immunodeficiency Virus
```

```
<400> SEQUENCE: 18

Ser Leu Tyr Asn Val Ala Thr Leu
 1               5

<210> SEQ ID NO 19
<211> LENGTH: 9
<212> TYPE: PRT
<213> ORGANISM: Human Immunodeficiency Virus

<400> SEQUENCE: 19

Ile Val Gly Ala Glu Thr Phe Tyr Val
 1               5
```